United States Patent
Takeuchi et al.

(10) Patent No.: US 7,153,831 B2
(45) Date of Patent: Dec. 26, 2006

(54) RABCONNECTIN-3-BINDING PROTEIN

(75) Inventors: Masakazu Takeuchi, Kyoto (JP); Yoshimi Takai, Kobe (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 11/257,883

(22) Filed: Oct. 25, 2005

(65) Prior Publication Data

US 2006/0040328 A1 Feb. 23, 2006

Related U.S. Application Data

(62) Division of application No. 10/645,335, filed on Aug. 21, 2003.

(30) Foreign Application Priority Data

Nov. 1, 2002 (JP) ............................. 2002-319521

(51) Int. Cl.
*A61K 38/00* (2006.01)
(52) U.S. Cl. ....................................................... 514/12
(58) Field of Classification Search ................... 514/12
See application file for complete search history.

(56) References Cited

FOREIGN PATENT DOCUMENTS

| EP | 0 856 583 | 8/1998 |
|---|---|---|
| JP | 10-276783 | 10/1998 |
| JP | 2001-309733 | 11/2001 |
| WO | WO 01/66739 A1 | 9/2001 |

OTHER PUBLICATIONS

Tanaka, et al., "Role of Rab3 GDP/GTP Exchange Protein in Synaptic Vesicle Trafficking at the Mouse Neuromuscular Junction", *Molecular Biology of the Cell*, 12: 1421-1430, 2001.
Wada, et al., "Isolation and Characterization of A GDP/GTP Exchange Protein Specific for the Rab3 Subfamily Small G Proteins", *The Journal of Biological Chemistry*, 272(7): 3875-3878, 1997.
Yamaguchi, et al., "A GDP/GTP Exchange Protein for the Rab3 Small G Protein Family Up-Regulates a Postdocking Step of Synaptic Exocytosis in Central Synapes", *PNAS*, 99(22): 14536-14541, 2002.
GenBank Accession No. AB011113, 1998.
GenBank Accession No. AC007052, 1999.
GenBank Accession No. AC008006, 2001.
GenBank Accession No. AF305813, 2000.
GenBank Accession No. XM028588, 2002.
Nagano, et al., "Molecular Cloning and Characterization of the Noncatalytic Subunit of the Rab3 Subfamily-Specific GTPase-Activating Protein", *The Journal of Biological Chemistry*, 273(38): 24781-74785, 1998.
Nagano, et al., "Rabconnectin-3, a Novel Protein that Binds Both GDP/GTP Exchange Protein and GTPase-Activating Protein for Rab3 Small G Protein Family", *The Journal of Biological Chemistry*, 277(12):9629-9632, 2002.
Nakanishi, et al., "Isolation of Regulatory Proteins for the Rab3 Subfamily GTPases", *Methods in Molecular Biology*, 189: 143-157, 2002.
Oishi, et al., "Localization of the Rab3 Small G Protein Regulators in Nerve Terminals and Their Involvement in $Ca^{2+}$—Dependent Exocytosis", *The Journal of Biological Chemistry*, 273(51): 34580-34585, 1998.
Sanders, et al., "Assignment of WDR7 (Alias TRAG, TGF-$\beta$ Resistance Associated Gene) to Orthologous Regions of Human Chromosome 18q21.1→q22 and Mouse Chromosome 18D.1-E.3 by Fluorescence in Situ Hybridization", *Cytogenet Cell Genet*, 88: 324-325, 2000.

*Primary Examiner*—Karen Cochrane Carlson
*Assistant Examiner*—Agnes B. Rooke
(74) *Attorney, Agent, or Firm*—Brenda Herschbach Jarrell; Charles E. Lyon; Choate Hall & Stewart, LLP

(57) ABSTRACT

A protein useful for clarifying the regulation mechanism of $Ca^{2+}$-dependent exocytosis in particular, the activation and inactivation of Rab3A, and a method of screening for a material useful for regulating $Ca^{2+}$-dependent exocytosis in particular, the activation and inactivation of Rab3A, using the above protein. By using the coimmunoprecipitation with an anti-Rab3A GEP antibody, a protein participated in the regulation of activation or inactivation of Rab3A is determined. As the protein binds to rabconnectin-3 and GDP/GTP exchange protein, it can be used for screening for a material that increases or decreases the binding.

4 Claims, 4 Drawing Sheets

RABCONNECTIN-3-BINDING PROTEIN

The present application is a Divisional application of co-pending application Ser. No. 10/645,335 filed Aug. 21, 2003 which claims priority to Japanese Application No. 2002-319521, filed on Nov. 1, 2002. The entire contents of each of the above listed applications are incorporated herein by reference.

BACKGROUND OF THE INVENTION

The present invention relates to a protein binding rabconnectin-3 and a GDP/GTP exchange protein, and a polynucleotide encoding the same.

Rab3A is a member of a Rab3 family consisting of four members: Rab3A, Rab3B, Rab3C, and Rab3D, and Rab3A is known to play a key regulatory role in $Ca^{2+}$-dependent exocytosis of neurotransmitters. The process of the $Ca^{2+}$-dependent exocytosis of neurotransmitters includes the following steps: (1) translocation of synaptic vesicles from the reserve pool to the active zone of the presynaptic plasma membrane where a $Ca^{2+}$ channel localizes, (2) docking of the vesicles to the active zone, (3) transition from the docking to the priming of the vesicles in the readily releasable pool, and (4) fusion of the vesicles with the membrane induced by $Ca^{2+}$ influx.

The analysis of Rab3A gene knockout mouse has revealed two actions of Rab3A: (1) it facilitates the translocation and docking of synaptic vesicles to the presynaptic plasma membrane, and (2) it prevents $Ca^{2+}$-triggered fusion of the vesicles with the plasma membrane. However, the molecular mechanism of these actions of Rab3A in the $Ca^{2+}$-dependent exocytosis of neurotransmitters is not known.

The Rab3 family members are regulated by three regulators: a GDP dissociation inhibitor (Rab GDI), a GDP/GTP exchange protein (Rab3 GEP), and a GTPase-activating protein (Rab3 GAP). Rab3 GEP and Rab3 GAP are specific for the Rab3 family members, but Rab GDI is active on all the Rab family members. The cyclical activation and inactivation of Rab3A by the action of these regulators are essential for the action of Rab3A in $Ca^{2+}$-dependent exocytosis of neurotransmitters. For example, a current model for the mode of action of these regulators is as follows: GDP-Rab3A is kept in the cytosol as a complex with Rab GDI. This complex is recruited to synaptic vesicles where GDP-Rab3A is activated to GTP-Rab3A by the action of Rab3 GEP with the help of another unidentified molecule, such as GDI displacement factor (GDF) for Rab5, Rab7, and Rab9, or Rab recycling factor (RRF) for Ypt1 and Ypt7. Neither GDF nor RRF has been isolated. GTP-Rab3A binds its two downstream effectors: rabphilin-3 and Rim-3 localized on the vesicles and the active zone, respectively. Before or after the fusion step, GTP-Rab3A in a complex with the effectors is inactivated to GDP-Rab3A by the action of Rab3 GAP. GDP-Rab3A is trapped by Rab GDI, resulting in the translocation from the vesicles to the cytosol. Thus, it is presumed that Rab3 GEP and Rab3 GAP are recruited to the vesicles when they function; however, their mechanisms remain unknown.

Recently, a novel protein was isolated from a crude synaptic vesicle (CSV) fraction of rat brain by coimmunoprecipitation with Rab3 GEP or Rab3 GAP, and was named rabconnectin-3 (see The Journal of Biological Chemistry, 2002, Vol. 277, No. 12, PP. 9629–9632). Human rabconnectin-3 consists of 3,036 amino acids and shows a calculated molecular weight of 339, 753. Rabconnectin-3 has 12 WD domains. Rabconnectin-3 is abundantly expressed in the brain where it is associated with the synaptic vesicles. Moreover, it has been found that further two proteins are coimmunoprecipitated with Rab3 GEP from a CSV fraction of rat brain (see The Journal of Biological Chemistry, 2002, Vol. 277, No. 12, PP. 9629–9632).

SUMMARY OF THE INVENTION

In one aspect, the invention provides protein useful for clarifying the regulation mechanism of $Ca^{2+}$-dependent exocytosis (in particular, the activation and inactivation of Rab3A. In another aspect, the invention provides a method of screening a material useful for regulating $Ca^{2+}$-dependent exocytosis (in particular, the activation and inactivation of Rab3A), using the above protein.

The inventors of the present invention have succeeded in obtaining a rabconnectin-3-binding protein that directly binds a GDP/GTP exchange protein.

In certain embodiments the present invention provides the following.

(1) A protein as defined in (a) or (b):
(a) a protein having the amino acid sequence of SEQ ID NO: 2; and
(b) a protein having the amino acid sequence of SEQ ID NO: 2 with one or several amino acids deleted, replaced, or added, and having an activity of binding rabconnectin-3 and a GDP/GTP exchange protein.

(2) A protein according to item (1) which has the amino acid sequence of SEQ ID NO: 2.

(3) A polynucleotide that encodes the protein as defined in item (1) or (2).

(4) A polynucleotide according to item (3), having a nucleotide sequence of nucleotide numbers 1 to 4470 of a nucleotide sequence of SEQ ID NO: 1.

(5) A polynucleotide as defined in (a) or (b):
(a) a polynucleotide having a nucleotide sequence of nucleotide numbers 1 to 4470 of a nucleotide sequence of SEQ ID NO: 1; and
(b) a polynucleotide which hybridizes with the polynucleotide having a nucleotide sequence that is complementary to the nucleotide sequence of nucleotide numbers 1 to 4470 of the nucleotide sequence of SEQ ID NO: 1 under a stringent condition, and encodes a protein having an activity of binding rabconnectin-3 and a GDP/GTP exchange protein.

(6) A polynucleotide as defined in (a) or (b):
(a) a polynucleotide having a nucleotide sequence of nucleotide numbers 1 to 4470 of a nucleotide sequence of SEQ ID NO: 1; and
(b) a polynucleotide having a nucleotide sequence whose homology to the nucleotide sequence of nucleotide numbers 1 to 4470 of the nucleotide sequence of SEQ ID NO: 1 is 80% or higher, and encoding a protein having an activity of binding rabconnectin-3 and a GDP/GTP exchange protein.

(7) A recombinant vector including the polynucleotide as defined in any one of items (3) to (6).

(8) A transformant obtained by transforming a host with the polynucleotide as defined in any one of items (3) to (6).

(9) A method of producing a protein having an activity of binding rabconnectin-3 and a GDP/GTP exchange protein, comprising:
culturing the transformant as defined in item (8) in a culture; and
collecting, from the culture, a protein having the activity of binding rabconnectin-3 and the GDP/GTP exchange protein.

(10) A use of a probe or a primer including a polynucleotide having at least 15 nucleotides complementary to the polynucleotide as defined in any one of items (3) to (6), which is adapted to detect the polynucleotide as defined in any one of items (3) to (6).

(11) A method of analyzing a first polynucleotide as defined in any one of items (3) to (6), comprising hybridizing a probe or a primer with the first polytnucleotide, wherein the probe or primer includes a second polynucleotide having at least 15 nucleotides complementary to the first polynucleotide.

(12) An analyzing method according to item (11), wherein the first polynucleotide is present in a tissue or a cell.

(13) A method of analyzing a first polynucleotide encoding the protein as defined in item (1) or (2), comprising hybridizing a probe or a primer with the first polynucleotide, wherein the probe or primer includes a second polynucleotide having at least 15 nucleotides complementary to the first polynucleotide.

(14) A method of analyzing a gene according to item (13), wherein the first polynucleotide is present in a tissue or a cell.

(15) A method comprising amplifying an mRNA in a tissue or a cell by an RT-PCR method with a primer that includes a polynucleotide having at least 15 nucleotides complementary to the polynucleotide as defined in any one of items (3) to (6).

(16) An antisense polynucleotide which hybridizes with an mRNA encoding the protein as defined in item (1) or (2).

(17) A ribozyme for cutting an mRNA encoding the protein as defined in item (1) or (2).

(18) A double-stranded RNA for cutting an mRNA encoding the protein as defined in item (1) or (2) by RNA interference.

(19) An antibody against the protein as defined in item (1) or (2).

(20) A method of immunohistologically analyzing the protein as defined in item (1) or (2), comprising contacting the protein with an antibody as defined in item (19).

(21) An analyzing method according to item (20), further comprising determining the location of the a protein.

(22) An analyzing method according to item (20), further comprising determining the amount of expression of the protein.

(23) A method of screening for a material that promotes or inhibits binding between a protein as defined in item (1) or (2) or a heterogeneous homologous protein thereof, and rabconnectin-3, comprising contacting the protein with rabconnectin-3 in the presence and absence of candidate materials, and selecting a material which increases or decreases the binding.

(24) A method of screening for a material that promotes or inhibits binding between a protein as defined in item (1) or (2) or a heterogeneous homologous protein thereof, and a Rab 3 GDP/GTP exchange protein, comprising contacting the protein with the Rab3 GDP/GTP exchange protein in the presence and absence of candidate materials, and selecting a material which increases or decreases the binding.

In other embodiments, the present invention provides a protein useful for clarifying the regulation mechanism of Ca$^{2+}$-dependent exocytosis (in particular, the activation and inactivation of Rab3A). In yet other embodiments, the present invention provides a method of screening for a material useful for regulating Ca$^{2+}$-dependent exocytosis (in particular, the activation and inactivation of Rab3A), using the above protein.

DETAILED DESCRIPTION OF THE INVENTION

<Protein, Etc. of the Present Invention>

Figure 1:
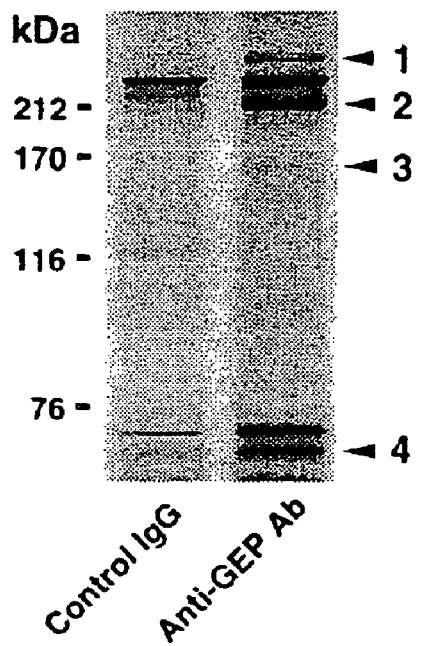
FIG. 1 shows isolation and a primary structure of p160 (rabconnectin-3β). (A) Results (electrophoresis photograph) of coimmunoprecipitation of p160 (rabconnectin-3β) with an anti-Rab3 GEP antibody. 1, p340; 2, p200; 3, p160; and 4, p60. (B) A schematic structure, wherein gray boxes represent WD domains. (C) Results (electrophoresis photograph) of Western blotting of recombinant rabconnectin-3β. Lane 1, HEK293 cells (1 μg of protein); lane 2, pCMVFa rabconnectin-3β-transfected HEK293 cells (1 μg of protein); and lane 3, homogenate of rat brain (20 μg of protein).
Figure 1:
Figure 1:
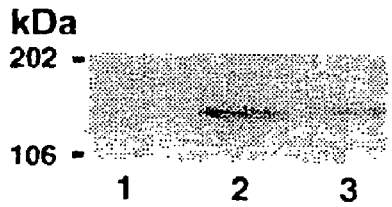

The protein of the present invention directly binds rabconnectin-3 and Rab3 GEP. The protein of the present invention forms a complex with rabconnectin-3. Therefore, hereinafter, the protein of the present invention will be also referred to as rabconnectin-3β, and rabconnectin-3 will be referred to as rabconnectin-3α.

Among the proteins of the present invention, the protein having an amino acid sequence of SEQ ID NO: 2 is a protein identified as human rabconnectin-3β, as described in the examples shown later. With respect to a protein, existence of a mutant having the same function is expected. Furthermore, by appropriately altering (for example, conservatively replacing) an amino acid sequence of a protein, a mutant having the same function can be obtained. Therefore, proteins having an amino acid sequence of SEQ ID NO: 2 with one or several amino acids deleted, replaced, or added and having an activity of binding rabconnectin-3 and a GDP/GTP exchange protein are also included in the protein of the present invention.

An amino acid sequence of a protein may be altered by altering a nucleotide sequence of a polynucleotide encoding the protein by well-known means such as a site-directed mutagenesis, and expressing the polynucleotide having the altered nucleotide sequence. Furthermore, the activity of binding rabconnectin-3 and a GDP/GTP exchange protein means binding them under a physiological condition, and this activity can be measured in accordance with a known method of measuring the binding between proteins (for example, see examples shown later, or "Protein Experiment Protocol Function Analysis", Shujunsha (1997), Chapter 9, Immunoprecipitation, Interaction Analysis Using Affinity Resin, pp. 151–161). Thus, it would be easy for those skilled in the art to determine whether or not a mutant has the same function.

An amino acid residue constituting the protein of the present invention may be a naturally occurring residue or a modified residue. Examples of the modification of an amino acid residue include acylation, acetylation, amidation, arginylation, GPI anchor formation, cross-linking, γ-carboxylation, cyclization, formation of a covalent cross-linkage, glycosylation, oxidation, covalent binding of a lipid or a fat derivative, formation of a disulfide bond, selenoylation, demethylation, decomposition of a protein, covalent binding of a nucleotide or a nucleotide derivative, hydroxylation, formation of pyroglutamate, covalent binding of flavin, prenylation, covalent binding of a heme moiety, covalent binding of phosphatidylinositol, formylation, myristoylation, methylation, ubiquitination, iodination, racemization, ADP-ribosylation, sulfation, phosphorization, etc. Furthermore, the protein of the present invention includes a precursor with a signal peptide portion, a mature protein lacking in a signal peptide portion, and a fusion protein modified by another peptide sequence. As the peptide sequence to be added to the protein of the present invention, a sequence (a vector such as pcDNA3.1/Myc-His (Invitrogen) can be used) facilitating the purification of a protein such as an influenza agglutinin (HA), glutathione S transferase (GST), substance P, poly histidine tag (6×His, 10×His, etc.), protein C fragment, maltose binding protein (MBP), immunoglobulin constant region, α-tubulin fragment, β-galactosidase, B-tag, c-myc fragment, E-tag (an epitope on a monoclonal phage), FLAG (Hopp et al. (1988) Bio/Technol. 6: 1204–10), lck tag, p18 HIV fragment, HSV-tag (a human herpes simplex virus glycoprotein), SV40T antigen fragment, T7-tag (T7 gene 10 protein), VSV-GP fragment (Vesicular stomatitis virus glycoprotein), etc., a sequence providing stability when a protein is produced by a recombinant technique, and the like can be selected.

The protein of the present invention can be produced by a known gene recombinant technique or a chemical synthesis method. In the case of producing the protein of the present invention by a gene recombinant technique, the protein to be produced may or may not be glycosylated and may further have different molecular weights, isoelectric points, etc., depending upon the kind of a host to be selected. Usually, in the case where the protein is expressed using a prokaryotic cell such as E. coli as a host, the protein to be obtained is produced with a methionine residue added to an N-terminus originally owned by the protein. The proteins having different structures due to the use of different hosts are also included in the protein of the present invention.

<Production of a Protein>

In the case of producing a protein in vitro, the protein can be produced in an in vitro system containing no cell in accordance with a method of in vitro translation (Dasso and Jackson (1989) Nucleic Acids Res. 17: 3129–44), etc. In contrast, in the case of producing a protein using cells, first, an appropriate host cell is selected, and transformed with an intended DNA. Then, the transformed cells are cultured, whereby a desired protein can be obtained. Culture is performed by a known method suitable for the selected cell. For example, in the case of selecting animal cells, a medium such as DMEM (Virology 8: 396 (1959)), MEM (Science 122: 501 (1952)), RPMI 1640 (J. Am. Med. Assoc. 199: 519 (1967)), 199 (Proc. Soc. Biol. Med. 73: 1 (1950)), IMDM, etc. is used with supplementation of a serum such as fetal calf serum (FCS), if required, and cultivation can be performed at pH of about 6 to 8 and at 30° C. to 40° C. for about 15 to 200 hours. In addition, if required, the medium can be exchanged in the course of culture, and aeration and stirring can be performed.

On the other hand, in order to establish an in vivo production system of a protein, an intended DNA is transduced to an animal or a plant, and a protein is produced in vivo. An animal system such as mammals (e.g., goat, pig, sheep, mouse, bovine, etc.), insects (e.g., silkworm) (Susumu (1985) Nature 315: 592–4), and the like are known (Lubon (1998) Biotechnol. Annu. Rev. 4: 1–54). Furthermore, a transgenic animal can also be used in a mammal system.

For example, in the case of allowing a desired protein to be secreted to milk of a goat, a DNA encoding the protein is bound to a DNA encoding a protein that is specifically secreted in milk such as β-casein, and the intended protein is expressed as a fusion protein. Then, the DNA encoding the fusion protein is transduced to the embryo of a goat. The DNA-transduced embryo is transplanted to the uterus of a female goat. A transgenic goat from the female goat or its offspring secretes a desired protein in milk. In order to increase the amount of milk, if required, hormones can be administered (Ebert et al. (1994) Bio/Technology 12: 699–702).

A protein-producing system of a transgenic plant using a plant such as tobacco is known. First, a DNA encoding a desired protein is integrated to a vector suitable for expression in a plant such as pMON530, and transduced to a bacterium such as Agrobacterium tumefaciens. A plant such as Nicotina tabacum is infected with the DNA-transduced bacterium to regenerate a plant, whereby the desired protein can be isolated from a leaf of the transgenic plant thus obtained (Julian et al. (1994) Eur. J. Immunol. 24: 131–8). Other methods have also been established: a method of transducing a DNA to a protoplast using PEG to regenerate a plant body (Gene Transfer to Plants, Potrykus and Spangenberg ed. (1995) pp. 66–74; suitable for indica rice); a method of transducing a DNA to a protoplast with an electric pulse to regenerate a plant body (Toki et al. (1992) Plant Physiol. 100: 1503–7; suitable for japonica rice); a method of transducing a DNA directly to a plant cell by a particle gun method to regenerate a plant body (Christou et al. (1991) Bio/Technology 9: 957–62); a method of transducing a DNA to a cell via Agrobacterium to regenerate a plant body (Hiei et al. (1994) Plant J. 6: 271–82), etc. Regarding the method of regenerating a plant, Toki et al. (1995) Plant Physiol. 100: 1503–7 can be referred to.

Once a transgenic plant is obtained, a plant host producing the protein of the present invention can be propagated similarly by using, as a material, a seed, a fruit, a tuber, a tuberous root, a root, a cut spike, a callus, a protoplast, or the like.

Usually, regarding the protein of the present invention produced by a gene recombinant technique, first, in the case where the protein is secreted extracellularly, a medium is collected, particularly, in the case of a transgenic organism, a body fluid, etc. is collected, and in the case where the protein is produced intracellularly, a lysate obtained by lysing the cells is collected. Then, as a method of purifying the protein, by appropriately combining known salting-out, distillation, various kinds of chromatography, gel electrophoresis, gel filtration, ultrafiltration, recrystallization, acid extraction, dialysis, immunoprecipitation, solvent precipitation, solvent extraction, ammonium sulfate or ethanol precipitation, etc., a desired protein is purified. As the chromatography, ion exchange such as anion or cation exchange, affinity, reversed phase, adsorption, gel filtration, hydrophobic, hydroxyapatite, phosphocellulose, lectin chromatography, and the like are known (Strategies for Protein Purification and Characterization: A Laboratory Course Manual, Marshak et al. ed., Cold Spring Harbor Laboratory Press (1996)). Liquid phase chromatography such as HPLC or FPLC can be used.

Furthermore, a naturally occurring protein may be purified. For example, a protein can be purified by affinity chromatography, using an antibody to the protein of the present invention (described later) (Current Protocols in Molecular Biology, John Wiley & Sons (1987) Section 16.1–16.19). Furthermore, a purification method can also be used which uses a glutathione column in the case of a fusion protein with GST and uses a nickel column in the case of a fusion protein with histidine tag added thereto. In the case of producing the protein of the present invention as a fusion protein, after purification, thrombin, factor Xa, or the like can be used to cut an unnecessary portion, if required. Furthermore, if required, the obtained polypeptide can be modified with an enzyme such as chymotrypsin, glucosidase, trypsin, protein kinase, lysyl endopeptidase, or the like.

<Polynucleotide>

The polynucleotide of the present invention encodes the protein of the present invention. This polynucleotide can be used when the protein of the present invention is expressed with a genetic engineering technique. Furthermore, the polynucleotide of the present invention can be used as a detection reagent of a rabconnectin-3-binding protein gene. That is, a molecular biological analysis can be performed, using a polynucleotide encoding the protein of the present invention or a partial specific fragment thereof, and a method of detecting a polynucleotide and a method of analyzing the amount of expression of the polynucleotide are provided. Examples of such methods include Southern blotting, Northern blotting, PCR, RT-PCR, quantitative RT-PCR, in situ hybridization, and the like.

In the present invention, it is confirmed that the rabconnectin-3-binding protein localizes in a synapse, so that the rabconnectin-3-binding protein can be used as a marker of a synapse. More specifically, a synapse can be detected by detecting the expression of a rabconnectin-3-binding protein gene, using a polynucleotide encoding the protein of the present invention or a partial specific fragment thereof. Thus, the polynucleotide of the present invention can be used as a synapse detection reagent. Furthermore, it is confirmed that the protein of the present invention binds rabconnectin-3 and a GDP/GTP exchange protein, so that the polynucleotide of the present invention can also be used for detecting rabconnectin-3 and the GDP/GTP exchange protein.

The term "polynucleotide" as used herein refers to a polymer composed of a plurality of bases or base pairs such as deoxyribonucleic acids (DNA) or ribonucleic acids (RNA), and includes a cDNA, a genomic DNA, chemically synthesized DNA, and RNA. The term "polynucleotide" also includes polynucleotides containing, if required, bases other than naturally occurring bases, such as 4-acetylcytidine, 5-(carboxyhydoxymethyl)uridine, 2'-O-methylcytidine, 5-carboxymethylaminomethyl-2-thiouridine, 5-carboxymethylaminomethyluridine, dihydrouridine, 2'-O-methylpseudouridine, β-D-galactosylqueuosine, 2'-O-methylguanosine, inosine, N6-isopentenyladenosine, 1-methyladenosine, 1-methylpseudouridine, 1-methylguanosine, 1-methylinosine, 2,2-dimehtylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, β-D-mannosylqueuosine, 5-methoxycarbonylmethyl-2-thiouridine, 5-methoxycarbonylmethyluridine, 5-methoxyuridine, 2-methylthio-N-6-isopentenyladenosine, N-((9-β-D-ribofuranosyl-2-methylthiopurin-6-yl)carbamoyl)threonine, N-((9-β-D-ribofuranosylpurin-6-yl)-N-methylcarbamoyl)-threonine, uridine-5-oxyacetic acid-methyl ester, uridine-5-oxyacetic acid, wybutoxosine, pseudouridine, queuosine, 2-thiocytidine, 5-methyl-2-thiouridine, 2-thiouridine, 4-thiouridine, 5-methyluridine, N-((9-β-D-ribofuranosylpurin-6-yl)carbamoyl)threonine, 2'-O-methyl-5-methyluridine, 2'-O-methyluridine, wybutosine, 3-(3-amino-3-carboxypropyl)uridine, and the like.

Examples of the polynucleotide of the present invention include a polynucleotide having a nucleotide sequence of nucleotide numbers 1–4470 of the nucleotide sequence of SEQ ID NO: 1. The nucleotide sequence of this polynucleotide is determined in the subsequent example. Furthermore, the polynucleotide of the present invention includes a nucleic acid sequence encoding the amino acid sequence of SEQ ID NO: 2 encoding the rabconnectin-3β protein, or a sequence complementary to the nucleic acid sequence. The nucleic acid sequence encoding such an amino acid sequence includes a nucleic acid sequence different from the sequence of SEQ ID NO: 1 due to the degeneracy of a genetic code, in addition to the nucleic acid sequence of SEQ ID NO: 1. In the case of using the polynucleotide of the present invention for expressing a polypeptide by a genetic engineering technique, a nucleotide sequence with a high expression efficiency can be selected and designed, by taking into consideration the codon usage frequency in a host to be used (Grantham et al. (1981) Nucleic Acids Res. 9: r43–74).

The polynucleotide of the present invention includes a nucleic acid sequence encoding the amino acid sequence of SEQ ID NO: 2 with one or several amino acids deleted, integrated, replaced, or added, and encoding the rabconnectin-3β protein or its antigenic fragment, or a sequence complementary to the nucleic acid sequence. It is known that, in a mutant polypeptide composed of an amino acid sequence with one or several amino acids deleted, integrated, replaced, or added, the same biological activity as that of the original polypeptide is maintained (Mark et al. (1984) Proc. Natl. Acad. Sci. USA 81: 5662–6; Zoller and Smith (1982) Nucleic Acids Res. 10: 6487–500; Wang et al. (1984) Science 224: 1431–3; Dalbadie-McFarland et al. (1982) Proc. Natl. Acad. Sci. USA 79: 6409–13). The several amino acids are generally 2 to 30, preferably 2 to 20, more preferably 2 to 10, and particularly preferably 2 to 5 amino acids.

Herein, the replacement of an amino acid denotes a mutation in which one and more amino acid residue in a sequence is replaced by a different kind of amino acid residue. In the case where an amino acid sequence encoded with the polynucleotide of the present invention is altered by such replacement, when it is necessary to retain the function of a protein, it is preferable to perform conservative replacement. Conservative replacement denotes changing a sequence so as to encode an amino acid having a similar property as that of an amino acid before replacement. Amino acids can be classified by their properties into, for example, nonpolar amino acids (Ala, Ile, Leu, Met, Phe, Pro, Trp, Val), uncharged amino acids (Asn, Cys, Gln, Gly, Ser, Thr, Tyr), acid amino acids (Asp, Glu), basic amino acids (Arg, His, Lys), neutral amino acids (Ala, Asn, Cys, Gln, Gly, Ile, Leu, Met, Phe, Pro, Ser, Thr, Trp, Tyr, Val), aliphatic amino acids (Ala, Gly), branched amino acids (Ile, Leu, Val), hydroxyamino acids (Ser, Thr), amide-type amino acids (Gln, Asn), sulfur-containing amino acids (Cys, Met), aromatic amino acids (His, Phe, Trp, Tyr), heterocyclic amino acids (His, Trp), imino acids (Pro, 4Hyp), and the like. Among them, replacement among Ala, Val, Leu, and Ile, between Ser and Thr, between Asp and Glu, between Asn and Gln, between Lys and Arg, and between Phe and Tyr is preferable for retaining the property of a protein. There is no particular limit to the number and site of amino acids to be altered, as long as an amino acid encoded by the polynucleotide has antigenicity of the rabconnectin-3β protein.

The polynucleotide encoding the amino acid sequence of SEQ ID NO: 2 with one or several amino acids deleted, integrated, replaced, or added can be prepared in accordance with a method such as a site-directed mutagenesis or the like described in "Molecular Cloning, A Laboratory Manual 2nd ed." (Cold Spring Harbor Press (1989)), "Current Protocols in Molecular Biology" (John Wiley & Sons (1987–1997); in particular, Section 8.1–8.5), Hashimoto-Goto et al. (1995) Gene 152: 271–5, Kunkel (1985) Proc. Natl. Acad. Sci. USA 82: 488–92, Kramer and Fritz (1987) Method. Enzymol. 154: 350–67, Kunkel (1988) Method. Enzymol. 85: 2763–6, and the like.

Furthermore, the polynucleotide of the present invention includes a nucleic acid sequence that hybridizes under a stringent condition to the nucleotide sequence of SEQ ID NO: 1 or a sequence complementary thereto and encodes the rabconnectin-3β protein or its antigenic fragment. As such a polynucleotide, an isoform, an alternative isoform, and an allelic mutant are conceived, and they are included in the polynucleotide of the present invention. Such a polynucleotide can be obtained from a cDNA library and a genome library of an animal such as a human being, a mouse, a rat, a rabbit, a hamster, a fowl, a pig, a bovine, a goat, or a sheep by a known hybridization method such as colony hybridization, plaque hybridization, or Southern blotting, using a polynucleotide composed of a nucleic acid sequence including SEQ ID NO: 1 or its fragment as a probe. Regarding a method of producing a cDNA library, "Molecular Cloning, A Laboratory Manual 2nd ed." (Cold Spring Harbor Press (1989)) can be referred to. Furthermore, commercially available cDNA libraries and genome libraries may be used.

More specifically, in production of a cDNA library, first, total RNA is prepared from cells, an organ, a tissue, or the like expressing the polynucleotide of the present invention, by a known method such as guanidine ultracentrifugation method (Chirwin et al. (1979) Biochemistry 18: 5294–9), or AGPC method (Chomczynski and Sacchi (1987) Anal. Biochem. 162: 156–9), and mRNA is purified using mRNA Purification Kit (Pharmacia) or the like. A kit for directly preparing mRNA such as a QuickPrep mRNA Purification Kit (Pharmacia) may also be used. Next, a cDNA is synthesized from the mRNA thus obtained, using a reverse transcriptase. A kit for cDNA synthesis such as an AMV Reverse Transcriptase First-strand cDNA Synthesis Kit (Seikagaku Corporation) is also commercially available. As the other methods, a cDNA may be synthesized and amplified by a 5'-RACE method using PCR (Frohman et al. (1988) Proc. Natl. Acad. Sci. USA 85: 8998–9002; Belyavsky et al. (1989) Nucleic Acids Res. 17: 2919–32). Furthermore, in order to produce a cDNA library having a high full length ratio, a known method such as an oligocap method (Maruyama and Sugano (1994) Gene 138: 171–4; Suzuki (1997) Gene 200: 149–56) or the like can be adopted. The cDNA obtained as described above is integrated to an appropriate vector.

The hybridization condition in the present invention is, for example, "2×SSC, 0.1% SDS, 50° C.", "2×SSC, 0.1% SDS, 42° C.", or "1×SSC, 0.1% SDS, 37° C.". A more stringent condition is, for example, "2×SSC, 0.1% SDS, 65° C.", "0.5×SSC, 0.1% SDS, 42° C.", "0.2×SSC, 0.1% SDS, 65° C.", and the like. More specifically, as a method using a Rapid-hyb buffer (Amersham Life Science), the following method can also be conceived. That is, prehybridization is performed at 68° C. for 30 minutes or more. Thereafter, a probe is added and kept at 68° C. for one hour or more to form a hybrid. Then, the hybrid is washed three times at room temperature for 20 minutes in 2×SSC (0.1% SDS), washed three times at 37° C. for 20 minutes in 1×SSC (0.1% SDS), and finally washed twice at 50° C. for 20 minutes in 1×SSC (0.1% SDS). Alternatively, the following may also be performed. For example, prehybridization is performed at 55° C. for 30 minutes or more in an Expresshyb Hybridization Solution (CLONTECH). A labeling probe is added. The mixture is incubated at 37° C. to 55° C. for one hour or more. Then, the hybrid is washed three times at room temperature for 20 minutes in 2× SSD (0.1% SDS), and washed once at 37° C. for 20 minutes in 1×SSC (0.1% SDS). Herein, for example, by increasing the temperature in prehybridization, hybridization, and the second washing, more stringent conditions can be obtained. For example, the temperature of prehybridization and hybridization can be set to be 60° C., and can be set to be 68° C. as a more stringent condition. Alternatively, hybridization is performed at 42° C. in 4×SSC containing 0.1% SDS, and washing is performed at 25° C. in 2×SSC containing 0.1% SDS (preferably 50° C. in 0.1×SSC containing 0.1% SDS) for one hour. Those skilled in the art would appropriately set various conditions such as a probe concentration, a probe length, and a reaction time, in addition to the conditions such as a salt concentration and a temperature of a buffer.

Regarding the detailed procedures of a hybridization method, "Molecular Cloning, A Laboratory Manual 2nd ed." (Cold Spring Harbor Press (1989); particularly, Section 9.47–9.58), "Current Protocols in Molecular Biology" (John Wiley & Sons (1987–1997); particularly, Section 6.3–6.4), "DNA Cloning 1: Core Techniques, A Practical Approach 2nd ed." (Oxford University (1995); particularly, Section 2.10 regarding the conditions), etc. can be referred to. Examples of a polynucleotide to be hybridized include a polynucleotide containing a nucleic acid sequence having the identity of at least 50% or more, preferably 70%, more preferably 80%, and still more preferably 90% (e.g., 95% or more, further preferably 99%) with respect to the nucleic acid sequence containing SEQ ID. No: 1. Such identity can be determined in accordance with a BLAST algorithm (Altschul (1990) Proc. Natl. Acad. Sci. USA 87: 2264–8; Karlin and Altschul (1993) Proc. Natl. Acad. Sci. USA 90: 5873–7). As a program based on this algorithm, BLASTX or the like has been developed as a program for determining the identity regarding an amino acid sequence, BLASTN or the like has been developed as a program for determining the identify regarding a nucleotide sequence (Altschul et al. (1990) J. Mol. Biol. 215: 403–10). These programs can be used for the sequence of the present invention. As a specific analysis method, for example, http://www.ncbi.nlm.nih.gov. etc. can be referred to.

In addition, a gene having a structure and a function similar to those of rabconnectin-3β, such as an isoform and an allelic mutant of rabconnectin-3β can be obtained from a cDNA library and a genome library of an animal such as a human being, a mouse, a rat, a rabbit, a hamster, a fowl, a pig, a bovine, a goat, or a sheep by designing primers based on the nucleic acid sequence of SEQ ID NO: 1, in accordance with a gene amplification technique (PCR) (Current Protocols in Molecular Biology, John Wiley & Sons (1987) Section 6.1–6.4).

The nucleotide sequence of the polynucleotide of the present invention can be confirmed by determining a sequence with a common method. For example, the confirmation of the nucleotide sequence can be performed by a dideoxynucleotide chain termination method (Sanger et al. (1977) Proc. Natl. Acad. Sci. USA 74: 5463) or the like. Furthermore, the sequence can be analyzed by using an appropriate DNA sequencer.

<Vectors>

According to the present invention, a vector containing the polynucleotide of the present invention is provided. The vector of the present invention is useful for holding the polynucleotide of the present invention in a host cell and expressing a polypeptide encoded by the polynucleotide. The vector of the present invention includes various vectors such as a plasmid, a cosmid, a virus, a bacteriophage, a cloning vector, and an expression vector (Molecular Cloning, A Laboratory Manual 2nd ed., Cold Spring Harbor Press (1989); Current Protocols in Molecular Biology, John Wiley & Sons (1987)). In a preferable embodiment, the polynucleotide of the present invention is operatively liked to a regulatory sequence so that the polynucleotide of the present invention is expressed in a host cell to which a vector is introduced. The term "regulatory sequence" as used herein includes a promoter, a ribosome binding site, and a terminator in the case where the host cell is a prokaryote and denotes a promoter and a terminator in the case where the host cell is an eukaryote. In some cases, the regulatory sequence may include a transactivator, a transcription factor, a poly(A) signal stabilizing a transcript, a splicing signal, a polyadenylation signal, and the like. Such a regulatory sequence contains all the constituents required for expressing a polynucleotide bound to the regulatory sequence. Furthermore, the vector of the present invention preferably includes a selectable marker. Further, a signal peptide, which is required for translocating a polypeptide expressed in the cells into an endoplasmic reticulum, a periplasm in the case where a Gram-negative bacteria is a host, or outside of the cell, may also be integrated to an expression vector so that it is added to an intended polypeptide. Furthermore, a linker may be added, and an initiation codon (ATG) and a termination codon (TAA, TAG or TGA) may be integrated, if required.

The vector of the present invention is preferably an expression vector. The term "expression vector" denotes a construct capable of expressing a polypeptide encoded in an expression vector in vitro or in an intended host cell. The expression vector of the present invention includes a cloning vector, a binary vector, an integrating vector, and the like. The expression process includes the transcription of a coding sequence in an expression vector to a translatable mRNA, translation from the mRNA to the polypeptide of the present invention, and in some cases, the secretion of the expressed polypeptide into an endoplasmic reticulum, a periplasm, or outside of the cell.

An example of a vector enabling the in vitro expression of a polypeptide includes pBEST (Promega). Furthermore, examples of a promoter enabling the expression in a prokaryotic cell host such as *E. coli* include $P_L$, araB (Better et al. (1988) Science 240: 1041–3), lacZ (Ward et al. (1989) Nature 341: 544–6; Ward et al. (1992) FASEB J. 6: 2422–7), trp, tac, trc (fusion of lac and trp), and the like. Furthermore, terminators derived from trpA, a phage, and rrnB ribosomal RNA can be used. Furthermore, an *E. coli* vector preferably includes "ori" for amplifying a vector in a host, and a marker gene for selecting a transformed host. It is preferable to use a drug-resistant gene capable of identifying a host with a drug such as ampicillin, tetracycline, kanamycin, or chloramphenicol. In particular, in the case of secreting a polypeptide to a periplasm, a pelB signal sequence (Lei et al. (1987) J. Bacteriol. 169: 4379) can be used. Examples of the vector include M13 vector, pUC vector, pBR322, pCR-Script, pGEX-5X-1 (Pharmacia), pEGFP, pBluescript (Stratagene), pET (Invitrogen: as the host in this case, BL21 expressing T7 polymerase is preferable), etc. In particular, examples of the vector for sub-cloning or cutting include pGEM-T, pDIRECT, pT7, etc.

An example of a host of bacteria other than *E. coli* includes *Bacillus*, such as pUB110 and pc194 vectors. More specifically, there are pPL608, pKTH50, and the like derived from *Bacillus subtilis*. In addition, vectors using, as a host, bacteria of *Pseudomonas* such as *Pseudomonas putida* and *Pseudomonas cepacia*; *Brevibacterium* such as *Brevibacterium lactofermentum* (pAJ43 (Gene 39: 281 (1985)), etc.); *Corynebacterium* such as *Corynebacterium glutamicum* (pCS11 (JP 57–183799 A; pCB101 (Mol. Gen. Genet. 196: 175 (1984)) etc.); *Streptococcus* (pHV1301 (FEMS Microbiol. Lett. 26: 239 (1985)); pGK1 (Appl. Environ. Microbiol. 50: 94 (1985)), etc.); *Lactobacillus* (pAMβ1 (J. Bacteiol. 137: 614 (1979)), etc.); *Rhodococcus* such as *Rhodococcus rhodochrous* (J. Gen. Microbiol. 138: 1003 (1992)); and *Streptomyces* such as *Streptomyces lividans* and *Streptomyces virginiae* (see Genetic Manipulation of *Streptomyces*: A Laboratory Manual, Hopwood et al., Cold Spring Harbor Laboratories (1985); pIJ486 (Mol. Gen. Genet. 203: 468–78 (1986)), pKC1064 (Gene 103: 97–9 (1991)), pUWL-KS (Gene 165: 149–50 (1995))) have been developed. Regarding a vector that can use a microorganism as a host, the documents such as "Microbiology Basic Course 8 Genetic Engineering" (KYORITSU SHUPPAN CO., LTD.) can be referred to. As procedures for transducing a vector to a bacterium host, a calcium chloride method (Mandel and Higa (1970) J. Mol. Biol. 53: 158–62; Hanahan (1983) J. Mol. Biol. 166: 557–80), electroporation method, and the like can be adopted.

Furthermore, examples of regulatory elements enabling the expression in a eucaryotic cell host include AOX1 and GAL1 promoters, in the case where yeast is used as a host. Examples of an expression vector derived from yeast include *Pichia* Expression Kit (Invitrogen), pNV11, SP-Q01, and the like. Vectors that can be used in yeast are described in Adv. Biochem. Eng. 43: 75–102 (1990), Yeast 8: 423–88 (1992), etc. More specifically, in *Saccharomyces* such as *Saccharomyces cerevisiae*, YRp, YEp, YCp, and YIp vectors can be used. In particular, an integration vector enabling a multicopy gene transduction and capable of holding a gene stably (EP537456, etc.) is useful. In addition, in *Kluyveromyces* such as *Kluyveromyces lactis*, 2 μm vector derived from *S. cerevisiae*, pKD1 vector (J. Bacteriol. 145: 382–90 (1981)), a vector derived from pGK11, *Kluyveromyces* autonomous replication gene KARS vector, and the like can be used. In *Schizosaccharomyces*, a vector described in Mol. Cell. Biol. 6: 80 (1986), and pAUR224 (Takara Shuzo Co., Ltd.) can be used. In *Zygosaccharomyces*, a vector derived from pSB3 (Nucleic Acids Res. 13: 4267 (1985)) can be used. In *Pichia* such as *Pichia angusta* or *Pichia pastoris*, a vector described in the document such as Yeast 7: 431–43 (1991), Mol. Cell. Biol. 5: 3376 (1985) or Nucleic Acids Res. 15: 3859 (1987) can be used. In *Candida* such as *Candida maltosa, C. albicans, C. tropicalis* or *C. utilis*, a vector described in JP 8-173170 A and a vector using ARS derived from *C. maltosa* (Agri. Biol. Chem. 51: 1587 (1987)) can be used. In *Aspergillus* such as *Aspergillus niger* and *A. oryzae*, a vector described in Trends in Biotechnology 7: 283–7 (1989) can be used. In *Trichoderma*, a vector using a promoter derived from extracellular cellulase gene (Bio/Technology 7: 596–603 (1989)) can be used.

In the case of using mammal and other animal cells as a host, adenovirus late promoter (Kaufman et al. (1989) Mol. Cell. Biol. 9: 946), CAG promoter (Niwa et al. (1991) Gene 108: 193–200), CMV immediate-early promoter (Seed and Aruffo (1987) Proc. Natl. Acad. Sci. USA 84: 3365–9), EF1α promoter (Mizushima et al. (1990) Nucleic Acids Res. 18: 5322; Kim et al. (1990) Gene 91: 217–23), HSV TK promoter, SRα promoter (Takebe et al. (1988) Mol. Cell. Biol. 8: 466), SV40 promoter (Mulligan et al. (1979) Nature 277: 108), SV40 early promoter (Genetic Engineering Vol. 3, Williamson ed., Academic Press (1982) pp. 83–141), SV40 late promoter (Gheysen and Fiers (1982) J. Mol. Appl. Genet. 1: 385–94), RSV (Rous sarcoma virus)-LTR promoter (Cullen (1987) Methods Enzymol. 152: 684–704), MMLV-LTR promoter, CMV enhancer, SV40 enhancer, globin intron, and the like can be used. Furthermore, it is preferable that a drug-resistant gene enabling the identification with a drug such as neomycin or G418 is included in a vector. In the case of increasing the copy number of genes in cells, for example, a vector such as pCHOI is adopted, which uses CHO lacking a nucleic acid synthesis pathway as a host and has a DHFR gene compensating for the lack, and the copy number can be increased by methotrexate (MTX). On the other hand, in order to temporarily express a gene, a vector can be used, which uses a COS cell having a T-antigen gene of SV40 on a chromosome as a host, and has a replication origin of SV40 such as pcD or a replication origin of adenovirus, bovine papilloma virus (BPV), polyoma virus, or the like. Furthermore, as a selection marker for increasing the gene copy number, genes encoding aminoglycoside transferase (APH), thymidinekinase (TK), xanthine guanine phosphoribosyl transferase (Ecogpt), dihydro folic acid reductase (dhfr) and the like may be included. As appropriate vectors, for example, an expression vector pcDV1 of Okayama-Berg (Pharmacia), pCDM8 (Nature 329: 840–2 (1987)), pRc/CMV, pcDNA1, pcDNA3 (Invitrogen), pSPORT1 (GIBCO BRL), pSV2dhfr (Mol. Cell. Biol. 1: 854–64 (1981)), pEF-BOS (Nucleic Acids Res. 18: 5322 (1990)), pCEP4 (Invitrogen), pMAM, pDR2, pBK-RSV, pBK-CMV, POPRSV, pOP13, pME18S (Mol. Cell. Biol. 8: 466–72 (1988)), etc. are known.

In particular, in order to express the polynucleotide of the present invention in an organism of an animal, adenovirus vector such as pAdexlcw and retrovirus vector such as pZIPneo can be used. A vector can be transduced to a host by an adenovirus method, an electroporation method (Cytotechnology 3: 133 (1990)), a cationic liposome method (Cationic Liposome DOTAP (Boehringer Mannheim), etc.), an transduction method with a positively charged polymer, an electrostatic type liposome method, an internal type liposome method, a method using a particle gun, a liposome method, lipofection, (Proc. Natl. Acad. Sci. USA 84: 7413 (1987)), a calcium phosphate method (JP 2-227075 A), a receptor-mediated gene transduction method, a retrovirus method, a DEAE dextran method, a virus-liposome method (Separate Volume, Experimental Medicine "Basic Technology of Gene Therapy", Yodosha Co., Ltd. (1997); Separate Volume, Experimental Medicine "Gene Transduction & Expression Analysis Experimental Method, Yodosha Co., Ltd. (1997); J. Clin. Invest. 93: 1458–64 (1994); Am. J. Physiol. 271: R1212–20 (1996); Molecular Medicine 30: 1440–8 (1993); Experimental Medicine 12: 1822–6 (1994); Protein Nucleic Acid Enzyme 42: 1806–13 (1997); Circulation 92 (Suppl. II): 479–82 (1995)), a naked-DNA direct transduction method, and the like. Virus vectors derived from virus other than adenovirus and retrovirus, for example, vectors produced based on Adeno-associated virus, Sindbis virus, Sendai virus, Togavirus, Paramyxovirus, Poxvirus, Poliovirus, Herpesvirus, Lentivirus, vaccinia virus, and the like can be used. Administration into an organism may be performed ex vivo or in vivo.

In addition, an insect expression system is also known as a system for expressing a heteropolypeptide. For example, an *Autographa california* nuclear polyhedrosis virus (Ac-NPV) is used as a vector, and a foreign gene can be expressed in *Spodoptera frugiperda* cells or *Trichoplusia larvae* cells. At this time, a target foreign gene is cloned in a non-essential region of virus. For example, the foreign gene may be operatively linked to a polyhedrin promoter. In this case, a polyhedrin gene is inactivated, and a recombinant virus lacking in a coat protein is produced. A target polypeptide is expressed in cells of *Spodoptera frugiperda, Trichoplusia larvae*, or the like infected with the virus (Smith (1983) J. Virol. 46: 584; Engelhard (1994) Proc. Natl. Acad. Sci. USA 91: 3227–7). In addition, as an expression vector derived from insect cells, Bac-to-BAC baculovirus expression system (Bigco BRL), pBacPAK8, and the like are known.

In the case of using plant cells as a host, for example, a vector utilizing a $^{35}S$ promoter of cauliflower mosaic virus or the like can be used. As a method of transducing a vector to plant cells, a PEG method, an electroporation method, an *Agrobacterium* method, a particle gun method, and the like are known.

A DNA can be inserted to a vector by a ligase reaction using a restriction enzyme site (Current Protocols in Molecular Biology, John Wiley & Sons (1987) Section 11.4–11.11; Molecular Cloning, A Laboratory Manual 2nd ed., Cold Spring Harbor Press (1989) Section 5.61–5.63).

<Transformant>

The transformant of the present invention is obtained by transforming a host with the polynucleotide of the present invention, and expresses the protein of the present invention.

<Host>

According to the present invention, a host containing the polynucleotide or vector of the present invention is provided. For production of the polypeptide of the present invention, in vitro and in vivo production systems are considered. The host of the present invention includes prokaryotic cells and eucaryotic cells derived from archaebacteria, bacteria, fungi, plants, insects, fishes, amphibians, reptiles, birds, and mammals. The host of the present invention includes a polynucleotide encoding the polypeptide of the present invention in cells. The polynucleotide should not be placed at a naturally occurring position on a genome of a host cell, and may be under the control of a promoter of the polynucleotide itself, transduced in a genome, and held as an extrachromosomal structure.

Examples of the bacterium host include Gram-positive and Gram-negative bacteria belonging to *Escherichia, Streptococcus, Staphylococcus, Serratia, Bacillus*, and the like, such as *E. coli* (JM109, DH5α, HB101, XL1Blue), *Serratia marcescens* and *Bacillus subtilis*.

The eucaryotic host includes cells such as fungi such as yeast, higher plants (cells derived from *Nicotiana tabacum*), insects (*drosophila* S2, *sporodoptera* Sf9, Sf21, Tn5), fishes, amphibians (*Xenopus laevis* oocyte (Valle et al. (1981) Nature 291: 358–40)), reptiles, birds, and mammals (CHO (J. Exp. Med. 108: 945 (1995); among them, a DHFR-gene deficient dhfr-CHO (Proc. Natl. Acad. Sci. USA 77: 4216–20 (1980) and CHO K-1 (Proc. Natl. Acad. Sci. USA 60: 1275 (1968)) are preferable), COS, Hela, C127, 3T3, BHK, HEK293, Bowes melanoma cells), myeloma, Vero, Namalwa, Namalwa KJM-1, HBT5637 (JP 63-299 A), and plants (potato, tobacco, corn, rice, oil-seed rape, soybean, tomato, wheat, barley, rye, alfalfa, flax, etc.). As the fungi, in addition to the yeast such as *Saccharomyces cerevisiae* belonging to *Saccharomyces* or one belonging to *Pichia*, an expression system using cells of *Aspergillus niger* belonging to *Aspergillus* of a filamentous fungi or the like is also known.

A vector is transduced to a host cell by an electroporation method (Chu et al. (1987) Nucleic Acids Res. 15: 1311–26), a cationic liposome method, an electric pulse perforation method (Current Protocols in Molecular Biology, John Wiley & Sons (1987) Section 9.1–9.9), a direct injection method using a minute glass tube, microinjection method, lipofection (Derijard (1994) Cell 7: 1025–37; Lamb (1993) Nature Genetics 5: 22–30; Rabindran et al. (1993) Science 259: 230–4), a lipofectamine method (GIBCO-BRL), a calcium phophate method (Chen and Okayama (1987) Mol. Cell. Biol. 7: 2745–52), a DEAE dextran method (Lopata et al. (1984) Nucleic Acids Res. 12: 5707–17; Sussman and Milman (1985) Mol. Cell. Biol. 4: 1642–3), FuGene 6 reagent (Boehringer-Mannheim), or the like.

The production method of the present invention is a method of producing the protein of the present invention, i.e., a rabconnectin-3-binding protein, and includes culturing the transformant of the present invention and collecting a rabconnectin-3-binding protein which is produced by the transformant from a culture. More specifically, the method described in the above-mentioned <Production of a protein> can be used.

Rabconnectin-3β and rabconnectin-3α are co-immuno-precipitated even with either one of an anti-rabconnectin-3α antibody and an anti-rabconnectin-3β antibody. Both the proteins are not separated from each other in the presence of 0.5 M NaCl or 1% CHAPS. However, they are partially separated from each other in the presence of 1 M NaCl, and completely separated from each other in the presence of 1% deoxycholate. Furthermore, these two proteins coexist in synaptic vesicles. These results show that rabconnectin-3α and -3β constitute a sub-unit structure.

It is shown that rabconnectin-3α does not have a trans-membrane portion, but binds to synaptic vesicles (see The Journal of Biological Chemistry, 2002, Vol. 277, No. 12, PP. 9629–9632). Rabconnectin-3α is separated from vesicles in the presence of a surfactant such as Triton X-100 and NP-40, which suggests that this protein is one of peripheral membrane proteins of synaptic vesicles. Similarly, rabconnectin-3β does not have a transmembrane portion, and is separated from vesicles in the same situation as the above, which suggests that this protein is also one of peripheral membrane proteins of synaptic vesicles.

Rabconnectin-3β directly binds to Rab3 GEP stoichio-metrically, whereas rabconnectin-3α does not bind. A complex of rabconnectin-3α and -3β directly binds to Rab3 GEP; however, this binding is much smaller than that of rabconnectin-3β in terms of stoichiometry. Therefore, this suggests that the interaction between 3α and 3β covers its binding site so that Rab3 GEP does not bind to the complex. In contrast, none of rabconnectin-3α, -3β, and a complex thereof binds to Rab3 GAP. This suggests that rabconnectin-3β indirectly binds to Rab3 GAP, probably via unidentified molecules.

The rabconnectin-3 and GDP/GTP exchange protein can be obtained as described in J. Biol. Chem., 272, 3875–3878 (1997), J. Biol. Chem., 273, 24781–24785, JP 10-210971 A, and the like.

<Probe>

According to the present invention, a probe with respect to the polynucleotide of the present invention is provided. The probe of the present invention is composed of a poly-nucleotide having at least 15 nucleotides complementary to the polynucleotide of the present invention. The term "complementary sequence" as used herein means not only ones in the form of at least 15 continued bases in a nucleotide sequence being completely paired with respect to a template, but also ones in the form of at least 70%, preferably 80%, more preferably 90%, and most preferably 95% or more (e.g., 97% or 99%) of the bases in the nucleotide sequence being paired. The term "paired bases" means that a chain is formed so that T (U in the case of RNA) corresponds to A, A corresponds to T or U, G corresponds to C, and C corresponds to G in a nucleotide sequence of a polynucleotide to be a template. The homology can be determined by the same method as that in the case of the above-mentioned polynucleotide to be hybridized. The probe of the present invention is preferably composed of a part of the polynucleotide of the present invention, i.e., a polynucleotide having at least 15 continued nucleotides. By using the probe of the present invention, the polynucleotide of the present invention can be detected or isolated. Furthermore, the expression of a gene encoding the protein of the present invention can be analyzed. Furthermore, the localization of the expression can be analyzed. Samples to be measured are organs, tissues, cells, and the like.

The analysis of the polynucleotide of the present invention or the analysis of the gene encoding the protein of the present invention, using a probe, can be performed by hybridizing the probe with a subject polynucleotide. Usually, it is performed by hybridizing a probe with a subject polynucleotide, detecting the hybrid thus obtained, and analyzing the detection result. The analysis of the detection result includes the measurement (including detection, quantitative determination) of the polynucleotide or the gene, and the detection of the localization of the polynucleotide or the gene. The subject polynucleotide may be present in a subject tissue or a subject cell.

<Primer>

According to the present invention, a primer with respect to the polynucleotide of the present invention is provided. Such a primer of the present invention is composed of a polynucleotide having at least 15 nucleotides complementary to the polynucleotide of the present invention, and can be used for detecting or amplifying the polynucleotide of the present invention. Usually, in the case where the polynucleotide is used as a primer, it is desirably composed of 15 to 100 bases, and preferably 15 to 35 bases. In the case where the polynucleotide is used as a primer, it is desirably composed of at least 15 bases, and preferably 30 bases. In the case of the primer, the nucleotide can be designed so as to have a structure in which the region on a 3'-terminus side is set to be a sequence complementary to a target sequence, and a restriction enzyme recognition sequence, tag, or the like is added to a 5'-terminus side. The primer of the present invention can be hybridized with the polynucleotide of the present invention. The primer of the present invention is preferably composed of a part of the polynucleotide of the present invention, i.e., a polynucleotide having at least 15 continued nucleotides. By using the primer of the present invention, the polynucleotide of the present invention can be detected or isolated. Furthermore, the expression of a gene encoding the protein of the present invention can be analyzed. Furthermore, the localization of the expression can be analyzed. Samples to be measured are organs, tissues, cells, and the like. Needless to say, mRNA can be amplified by RT-PCR, using these primers. Furthermore, mRNA in a sample can also be quantified by quantitative RT-PCR.

The analysis of the polynucleotide of the present invention or the analysis of the gene encoding the protein of the present invention, using a primer, can be performed by hybridizing the primer with a subject polynucleotide. Usually, it is performed by hybridizing a primer with a subject polynucleotide to amplify the polynucleotide (i.e., PCR is performed using a primer, with the subject polynucleotide (reverse transcription is performed, if required) being a template, detecting an amplified product, and analyzing the detection results. The analysis of the detection result includes the measurement (including detection and quantitative determination) of the polynucleotide or the gene, and the detection of the localization of the polynucleotide or the gene. The subject polynucleotide may be present in a subject tissue or a subject cell.

<Antisense>

According to the present invention, an antisense polynucleotide with respect to the polynucleotide of the present invention is provided. The antisense polynucleotide of the present invention suppresses the expression of the polynucleotide of the present invention in cells by binding mRNA or DNA.

The mechanisms of suppressing the expression of a target gene by an antisense polynucleotide may be as follows: (1) inhibition of transcription initiation by forming a triple helix, (2) suppression of transcription by forming a hybrid with a local open-loop structure site formed by RNA polymerase, (3) inhibition of transcription by forming a hybrid with RNA in the course of synthesis, (4) suppression of splicing by forming a hybrid at a junction point of intron-exon, (5) suppression of splicing by forming a hybrid with a spliceosome forming site, (6) suppression of transition of mRNA to a cytoplasm by forming a hybrid with mRNA, (7) suppression of splicing by forming a hybrid with a capping site or a poly-A addition site, (8) suppression of translation initiation by forming a hybrid with a translation initiation factor binding site, (9) suppression of translation by forming a hybrid with a ribosome binding site, (10) suppression of elongation of a peptide chain by forming a hybrid with an mRNA translation region or a polysome binding site, and (11) suppression of gene expression by forming a hybrid with an interaction site of a nucleic acid and a protein (Hirashima and Inoue, "New Biochemistry Experimental Course 2, Nucleic Acid IV, Replication and Expression of Gene", edited by Nihon Seikagaku-kai, Tokyo Kagaku Dojin, pp. 319–347 (1993)).

The antisense polynucleotide included in the present invention may suppress the expression of a gene by any of the above mechanisms (1) to (11). More specifically, the antisense polynucleotide may include an antisense sequence with respect to a sequence in a non-translation region, as well as a translation region of a gene intended to be inhibited for expression. DNA encoding an antisense polynucleotide can be used by operatively linking it to an appropriate regulatory sequence enabling the expression. It is not necessarily required that the antisense polynucleotide is completely complementary to a translation region or a non-translation region of a target gene, and only needs to inhibit the expression of the gene effectively. Such an antisense polynucleotide has a chain length of at least 15 bp, preferably 100 bp or more, more preferably 500 bp or more, generally 3000 bp or less, preferably 2000 bp or less, and more preferably 1000 bp or less, and has a homology of preferably 90% or more, and more preferably 95% or more with respect to a complementary chain of a transcript product of the target gene. Such an antisense polynucleotide can be prepared by a phosphorothionate method (Stein (1988) Nucleic Acids Res. 16: 3209–21), etc. based on the polynucleotide of the present invention.

<Ribozyme>

According to the present invention, a ribozyme with respect to the polynucleotide of the present invention is provided. The ribozyme of the present invention suppresses the expression of the polynucleotide of the present invention in cells by binding mRNA or DNA.

The ribozyme is a generic name for catalysts containing RNA as a constituent component, and is roughly classified into large ribozyme and small ribozyme. The large ribozyme is a enzyme which cuts a phosphate bond of a nucleic acid, and leaves 5'-phosphoric acid and 3'-hydroxyl group at a reaction site after reaction. The large ribozyme is further classified into (1) group I intron RNA that performs trans-esterification at a 5'-splice site with guanosine, (2) group II intron RNA that performs self-splicing in two-stage reactions through a lariat structure, and (3) a RNA component of ribonucrease P that cuts a tRNA precursor on a 5'-side by hydrolysis. In contrast, the small ribozyme is a relative small structural unit (about 40 bp), and cuts an RNA to generate a 5'-hydroxyl group and 2'-3' cyclic phosphoric acid. The small ribozyme includes ribozymes of a hammer head type (Koizumi et al. (1988) FEBS Lett. 228: 225), a hairpin type (Buzayan (1986) Nature 323: 349; Kikuchi and Sasaki (1992) Nucleic Acids Res. 19: 6751; Hiroshi Kikuchi (1992) Chemistry and Biology 30: 112), and the like. Regarding the ribozyme, various modified methods are known, since the ribozyme is altered and synthesized easily. For example, by designing the ribozyme so that a substrate binding portion thereof is complementary to a RNA sequence close to a target site, a hammer head type ribozyme can be produced, which recognizes and cuts a basic sequence UC, UU, or UA in a target RNA (Koizumi et al. (1988) FEBS Lett. 228: 225; Makoto Koizumi and Eiko Ohtsuka (1990) Protein nucleic acid enzyme 35: 2191; Koizumi et al. (1989) Nucleic Acids Res. 17: 7059). The hair pin type ribozyme can also be designed and produced in accordance with a known method (Kikuchi and Sasaki (1992) Nucleic Acids Res. 19: 6751; Hiroshi Kikuchi (1992) Chemistry and Biology 30: 112).

The antisense polynucleotide and ribozyme of the present invention can also be used for gene therapy with ex vivo method or in vivo method, as a vector derived from virus such as retrovirus, adenovirus, and adeno-associated virus, a non-virus vector using liposome or the like, or naked DNA, in order to regulate the expression of a gene in cells.

The nucleotide sequence of the antisense polynucleotide and ribozyme of the present invention can be confirmed by the same method as that of the polynucleotide described above.

<RNA Interference>

According to the present invention, a double-stranded RNA that makes a cut by RNA interference with respect to the polynucleotide of the present invention is provided. The double-stranded RNA of the present invention suppresses the expression of the polynucleotide of the present invention in cells by binding an mRNA and being cut enzymatically (Fire et al. (1998) Nature 391: 806–811; Takashi Morita et al., (2002) Protein, Nucleic acid, Enzyme 47: 1939–1945).

The double-stranded RNA of the present invention can also be used for gene therapy with ex vivo method or in vivo method, as a vector derived from virus such as retrovirus, adenovirus, adeno-associated virus, a non-virus vector using liposome or the like, or naked DNA, in order to regulate the expression of a gene in cells.

The antisense polynucleotide and ribozyme of the present invention, and the double-stranded RNA that makes a cut by RNA interference with respect to the polynucleotide of the present invention can reduce an mRNA encoding the protein of the present invention. Thus, they can reduce the protein of the present invention. Furthermore, the antisense polynucleotide and ribozyme of the present invention, and the double-stranded RNA that makes a cut by RNA interference with respect to the polynucleotide of the present invention function as an inhibition reagent of the rabconnectin-3-binding protein, so that they are useful as a reagent for analyzing the function of the protein of the present invention.

In the present invention, it is confirmed that the rabconnectin-3-binding protein localizes in a synapse, and binds rabconnectin-3 and a GDP/GTP exchange protein. Based on this, it is considered that the rabconnectin-3-binding protein participates in the regulation of the transportation of synaptic vesicles. Therefore, the material inhibiting the rabconnectin-3-binding protein may participate in diseases considered to be caused by the abnormality of the transportation of synaptic vesicles (e.g., intellectual disorder (mental retardation), attention deficit hyperactivity disorder, autistic disorder, learning disorder, etc.). Thus, the antisense polynucleotide and ribozyme of the present invention, and the double-stranded RNA that makes a cut by RNA interference with respect to the polynucleotide of the present invention can be used as an effective ingredient of therapeutic agents for these diseases having an inhibition action to the protein of the present invention.

<Antibody>

According to the present invention, an antibody to the polypeptide of the present invention or its polypeptide fragment is provided. The antibody of the present invention includes a polyclonal antibody, a monoclonal antibody, a chimera antibody, a single-stranded antibody (scFV) (Huston et al. (1988) Proc. Natl. Acad. Sci. USA 85: 5879–83; The Pharmacology of Monoclonal Antibody, Vol. 113, Rosenburg and Moore ed., Springer Verlag (1994) pp. 269–315), a humanized antibody, a multispecific antibody (LeDoussal et al. (1992) Int. J. Cancer Suppl. 7: 58–62; Paulus (1985) Behring Inst. Mitt. 78: 118–32; Millstain and Cuello (1983) Nature 305: 537–9; Zimmermann (1986) Rev. Physiol. Biochem. Pharmacol. 105: 176–260; Van Dijk et al. (1989) Int. J. Cancer 43: 944–9), and antibody fragments such as Fab, Fab', F(ab')2, Fc, and Fv. Furthermore, the antibody of the present invention may be modified with PEG or the like, if required. In addition, the antibody of the present invention may be produced as a fusion protein with β-galactosidase, a maltose binding protein, GST, a green fluorescent protein (GFP), etc., and may be designed so as to be detected without using a secondary antibody. Furthermore, the antibody of the present invention may be altered by labeling an antibody with biotin, etc. so as to enable collection of an antibody using avidin, streptoavidin, etc.

The antibody of the present invention can be produced using the polypeptide of the present invention or a fragment thereof, or cells expressing them as a sensitized antigen. Furthermore, the polypeptide of the present invention or a short fragment thereof may bind a carrier such as bovine serum albumin, keyhole limpet hemocyaninm, ovalbumin, etc. to be used as an immunogen. Furthermore, known adjuvants such as an aluminum adjuvant, complete (or incomplete) Freund's adjuvant, pertussis adjuvant, and the like can be used for enhancing an immune response to an antigen, together with the polypeptide of the present invention or its fragment.

A polyclonal antibody is obtained, for example, as follows: a mammal is immunized with the polypeptide of the present invention or a fragment thereof, together with a desired adjuvant, and serum is obtained from the immunized animal. There is no particular limit to mammals used here and animals of rodentia, lagomorpha, and primates are generally used. Examples of the mammals include rodentia such as a mouse, a rat, a hamster, etc.; lagomorpha such as a rabbit; and primates such as monkeys (e.g., crab-eating monkey, rhesus monkey, hamadryad, chimpanzee, etc.). An animal is immunized by injecting the animal with the solution thus obtained intraperitoneally or subcutaneously after appropriately diluting and suspending a sensitization antigen in phosphate-buffered saline (PBS), a saline, etc., and optionally mixing an adjuvant with the resultant solution, to emulsify the solution. Thereafter, preferably, the sensitization antigen mixed with Freund's complete adjuvant is administered to the animal several times every 4 to 21 days. The production of an antibody can be confirmed by measuring a desired antibody level in the serum by a conventional method. Finally, the serum itself may be used as a polyclonal antibody, or may be further purified. Regarding a specific method, for example, "Current Protocols in Molecular Biology" (John Wiley & Sons (1987) Section 11.12–11.13) can be referred to.

In order to produce a monoclonal antibody, first, the spleen is isolated from an animal immunized in the above-mentioned manner, an immunocytes are separated from the spleen, and the immunocytes are fused with appropriate myeloma cells, using polyethylene glycol (PEG) or the like to prepare hybridomas. The fusion of the cells can be performed in accordance with a method of Milstein (Galfre and Milstein (1981) Methods Enzymol. 73: 3–46). Herein, in particular, examples of appropriate myeloma cells include those which enable fused cells to be selected with a drug. In the case of using such myelomas, the fused hybridomas are selected by culture in a culture medium (HAT medium) containing hypoxanthine, aminopterin, and thymidine in which cells other than the fused cells will die. Then, a clone producing an antibody that binds the polypeptide of the present invention or a fragment thereof is selected from the hybridoma thus prepared. Thereafter, the selected clone is implanted to the abdominal cavity of a mouse or the like, and ascites is collected to obtain a monoclonal antibody. Furthermore, regarding a specific method, "Current Protocols in Molecular Biology" (John Wiley & Sons (1987) Section 11.4–11.11) can be referred to.

A hybridoma can also be obtained by a method of sensitizing human lymphocytes infected with EB virus in vitro, using an immunogen, fusing the sensitized lymphocytes with myeloma cells derived from a human being (U266, etc.), thereby obtaining a hybridoma that produces a human antibody (JP 63-17688 A). Furthermore, a human antibody can also be obtained by using antibody-producing cells prepared by sensitizing a transgenic animal having a repertoire of a human antibody gene (WO92/03918; WO93/02227; WO94/02602; WO94/25585; WO96/33735; WO96/34096; Mendez et al. (1997) Nat. Genet. 15: 146–56, etc.). An example that does not use a hybridoma includes a method of transducing a cancer gene to an immunocyte such as lymphocyte and the like producing an antibody, thereby making the immunocyte immortal.

Furthermore, an antibody can be produced by genetic engineering (see Borrebaeck and Larrick (1990) Therapeutic Monoclonal Antibodies, MacMillan Publishers LTD., UK). In order to produce an antibody, first, a gene encoding an antibody is cloned from a hybridoma or antibody-producing cells (sensitized lymphocytes, etc.). The gene thus obtained is integrated in an appropriate vector, the vector is transduced to a host, and the host is cultured, whereby an antibody is produced. Such a recombinant antibody is also included in the antibody of the present invention. Representative examples of the recombinant antibody include a chimera antibody composed of a variable region derived from a non-human antibody and a constant region derived from a human antibody, and humanized antibody composed of a complementary determining region derived from a non-human antibody (CDR), a framework region (FR) derived from a human antibody, and a constant region (Jones et al. (1986) Nature 321: 522–5; Reichmann et al. (1988) Nature 332: 323–9; Presta (1992) Curr. Op. Struct. Biol. 2: 593–6; Methods Enzymol. 203: 99–121 (1991)).

The antibody fragment of the present invention can be produced by treating the above-mentioned polyclonal or monoclonal antibody with an enzyme such as papain or pepsin. Alternatively, the antibody fragment of the present invention can also be produced in a genetic engineering manner, using a gene encoding an antibody fragment (see Co et al., (1994) J. Immunol. 152: 2968–76; Better and Horwitz (1989) Methods Enzymol. 178: 476–96; Pluckthun and Skerra (1989) Methods Enzymol. 178: 497–515; Lamoyi (1986) Methods Enzymol. 121: 652–63; Rousseaux et al. (1986) 121: 663–9; Bird and Walker (1991) Trends Biotechnol. 9: 132–7).

The multispecific antibody of the present invention includes a bispecific antibody (BsAb), a diabody (Db), and the like. The multispecific antibody can be produced by a method of: (1) chemically coupling different specific antibodies to each other with a hetero-bifunctional linker (Paulus (1985) Behring Inst. Mill. 78: 118–32); (2) fusing a hybridoma that secretes different monoclonal antibodies (Millstein and Cuello (1983) Nature 305: 537–9); (3) transfecting an eucaryotic cell expression system such as mouse myeloma cells with light chain and heavy chain genes (four kinds of DNAs) of different monoclonal antibodies, and thereafter isolating a monovalent portion of a bispecific antibody (Zimmermann (1986) Rev. Physio. Biochem. Pharmacol. 105: 176–260; Van Dijk et al. (1989) Int. J. Cancer 43: 944–9); or the like. On the other hand, Db is an antibody fragment of a dimmer composed of two divalent polypeptide chains that can be configured by gene fusion, and can be produced by known procedures (see Holliger et al. (1993) Proc. Natl. Acad. Sci. USA 90: 6444–8; EP404097; WO93/11161).

The collection and purification of an antibody and an antibody fragment can also be performed by using proteins A and G, and by a protein purification technique described in detail in <Production of a protein> (Antibodies: A Laboratory Manual, Ed Harlow and David Lane, Cold Spring Harbor Laboratory (1988)). For example, in the case of using protein A for purifying the antibody of the present invention, a protein A column such as Hyper D, POROS, and Sepharose F. F. (Pharmacia) is known and can be used. The concentration of the thus-obtained antibody can be determined by measuring its absorbance or by enzyme-linked immunosorbent assay (ELISA), etc.

The antigen binding activity of an antibody can be measured by absorbance measurement, a fluorescent antibody method, enzyme immunoassay (EIA), radioimmunoassay (RIA), ELISA, or the like. In the case of measuring the antigen binding activity by ELISA, the antibody of the present invention is immobilized on a carrier such as a plate, the polypeptide of the present invention is added to the plate, and a sample containing an intended antibody is added thereto. Herein, as a sample containing an antibody, a culture supernatant of antibody-producing cells, a purified antibody, and the like are considered. Then, a secondary antibody recognizing the antibody of the present invention is added to the plate, and the plate is incubated. Thereafter, the plate is washed, and a label added to the secondary antibody is detected. More specifically, in the case where the secondary antibody is labeled with alkali phosphatase, a substrate of the enzyme such as p-nitrophenyl phosphate is added to the plate to measure the absorbance, whereby the antigen binding activity can be measured. Furthermore, a commercially available system such as BIAcore (Pharmacia) can also be used for the evaluation of the activity of an antibody.

The antibody of the present invention can be used as a reagent for detecting the rabconnectin-3-binding protein. That is, an immunohistological analysis method can be performed using the antibody of the present invention. Thus, the present invention provides an immunohistological analysis method, e.g., a method of analyzing the expression amount of a protein and a method of analyzing the localization of a protein. Examples of the immunohistological analysis method include enzyme immunoassay (EIA), radioimmunoassay (RIA), ELISA, Western blotting, flow cytometry, immunohistochemical staining, and the like. Furthermore, the antibody of the present invention can be used for purifying the polypeptide of the present invention and a fragment thereof.

According to the present invention, it is confirmed that the rabconnectin-3-binding protein localizes in a synapse. Based on this, the detection using the antibody of the present invention can also be performed, using the rabconnectin-3-binding protein as a marker of a synapse. Thus, the antibody of the present invention can be used as a reagent for detecting a synapse, if required. Furthermore, it is confirmed that the protein of the present invention binds rabconnectin-3 and a GDP/GTP exchange protein. Therefore, the antibody of the present invention can be used for detecting them.

<Screening Method of the Present Invention>

The protein of the present invention binds rabconnectin-3 and a Rab3 GDP/GTP exchange protein. Thus, the protein of the present invention can be used for screening a material that increases or decreases the binding. Although the protein of the present invention is derived from a human being, a heterogeneous homologous protein having the same activity as that of the protein of the present invention, which is present in other species such as a rat, can also be used for the above purpose in the same way as in the protein of the present invention. Thus, there is provided a method of screening a candidate material for promoting or inhibiting the binding between the protein of the present invention or the rabconnectin-3-binding protein that is a heterogeneous homologous protein thereof and rabconnectin-3, comprising: reacting the rabconnectin-3-binding protein and rabconnectin-3 with each other in the presence and absence of the candidate material, and selecting the candidate material that increases or decreases the binding. There is also provided a method of screening a candidate material for promoting or inhibiting the binding between the protein of the present invention or the Rab3 GDP/GTP exchange protein-binding protein that is a heterogenous homologous protein thereof, and the Rab3 GDP/GTP exchange protein, comprising: reacting the Rab3 GDP/GTP exchange protein-binding protein and the Rab3 GDP/GTP exchange protein with each other in the presence and absence of the candidate material, and selecting the candidate material that increases or decreases the binding.

The measurement of the binding between the rabconnectin-3-binding protein and rabconnectin-3, and the binding between the Rab3 GDP/GTP exchange protein-binding protein and the Rab3 GDP/GTP exchange protein can be performed in accordance with a known method of measuring the binding between the proteins.

It is considered that the protein of the present invention and a heterogeneous homologous protein thereof, that is P160, participate in the regulation of the transportation of synaptic vesicles such as neurotransmitter release and the like. Therefore, it is considered that the material thus selected, which promotes or inhibits the binding, can be used as an active ingredient for a therapeutic agent for diseases (e.g., intellectual disorder (mental retardation), attention deficit hyperactivity disorder, autistic disorder, learning disorder, etc.) caused by the abnormality of the transportation of the synaptic vesicles.

Such therapeutic agents (pharmaceuticals) can be produced by preparing a material (active ingredient) selected by screening. Preparation can be performed appropriately in accordance with a conventional method, depending upon the kind of the selected material, the type of preparation, etc. The pharmaceuticals may be included a pharmaceutical composition comprising an active constituent and a pharmaceutically acceptable carrier.

EXAMPLES

The present invention will be described in detail by way of the following examples. It should be noted that the present invention is not limited to the examples.

Example 1

(1) Preparation of Rat Proteins Coimmunoprecipitated with Rab3 GEP

A CSV fraction extract of rat brain was coimmunoprecipitated with an anti-Rab3 GEP antibody in accordance with a method described in J. Biol. Chem., 277, 9629–9632 (2002), and a precipitate was electrophoresed. More specifically, a CSV fraction was prepared from rat brain as described in the above document. The fraction was extracted with Buffer A (20 mM Tris/HCl (pH 7.5), 1 mM EDTA, 1 mM DTT, 0.8% n-octylglucopyranoside), and the extract was incubated overnight at 4° C. with the anti-Rab3 GEP antibody immobilized on protein A Sepharose beads (20 μl wet weight). After the beads were extensively washed with Buffer A, bound proteins were eluted by boiling the beads in an SDS sample buffer (60 mM Tris/HCl (pH 6.7), 3% SDS, 2% (v/v) 2mercaptoethanol, 5% glycerol). The sample was subjected to SDS-PAGE, followed by the protein staining. Consequently, two proteins (Band No. 2) coimmunoprecipitated with Rab3 GEP, as well as rabconnectin-3 (Band No. 1), p160 (Band No. 3), and p60 (Band No. 4), were detected (A in FIG. 1).

Band No. 3 was cut out from the gel and digested with trypsin, and the peptides were subjected to mass spectrometric analysis. Computer database search revealed that p160 includes an amino acid sequence deduced from a human cDNA fragment (KIAA0541, GenBank accession No. AB011113).

As described in the following (5), p160 was found to form a complex with rabconnectin-3. Therefore, hereinafter, p160 and rabconnectin-3 will be referred to as rabconectin-3β and rabconectin-3α, respectively.

(2) Molecular Cloning and Determination of Primary Structure

KIAA0541 cDNA contained a coding region of about 3.5 kb and an inframe stop codon, but lacked a predicted initiation codon. Furthermore, the sequence of KIAA0541 cDNA was included in BAC clones of the human genome (GenBank Accession Nos. AC007052 and AC008006). On the basis of this information, PCR was performed so as to obtain a 5'-terminus region of human rabconnectin-3β cDNA. More specifically, a set of primers having sequences: ATG GCA GGA AAC AGC CTT GTT CTA CCC ATT GTT C (SEQ ID NO: 3)/GTT GTC ATT GCC AGC CCT TCT TCA CTT CCC (SEQ ID NO: 4) was designed. A cDNA fragment was amplified using these primers from a human heart cDNA (CLONTECH). A PCR product was subcloned to a pCR4 Blunt vector (Invitrogen). DNA sequencing was performed by a dideoxy nucleotide termination method using a DNA sequencer (ABI PRISM 3100 Genetic Analyzer, PE Biosystems). As a result, a cDNA fragment containing about a 1.0 kb coding region and a predicted initiation codon was obtained.

The full length of human rabconnectin-3β cDNA was obtained by ligation of the above cDNA fragment to KIAA0541 cDNA (SEQ ID NO: 1). A encoded protein consisted of 1,490 amino acids, and showed a calculated molecular weight of 163, 808 (SEQ ID NO: 2). The human rabconnectin-3β contained 7 WD domains (B in FIG. 1). In order to confirm whether the ligated cDNA encodes the full-length human rabconnectin-3β, the cDNA was transfected into HEK293 cells. The cell extract was subjected to SDS-PAGE, followed by Western blotting with an anti-rabconnectin-3β antibody. More specifically, pCMVFa rabconnectin-3β (see the following (3)) was transfected into HEK293 cells, a lysate of the cells was subjected to SDS-PAGE (10% polyacrylamide gel), followed by Western blotting with an anti-rabconnetin-3β-1 antibody (see the following (3)). As a control, the HEK293 cell lysate and homogenate of rat brain were similarly subjected to SDS-PAGE, followed by the Western blotting. As a result, a protein with a molecular weight of about 160 kDa was detected (C in FIG. 1). In C of FIG. 1, each lane was as follows: Lane 1, control HEK293 cells (1 μg protein); Lane 2, pCMVFa rabconectin-3β-transfected HEK293 cells (1 μg protein); and Lane 3, homogenate of rat brain (20 μg protein).

The above-mentioned molecular weight was the same as that of native rabconnective-3β derived from rat brain. Therefore, it was concluded that the cDNA encodes the full length of the human rabconnectin-3β. The human rabconnectin-3β showed a domain structure similar to rat TRAG (GenBank Accession No. AF305813) and human WDR7 (GenBank Accession No. XMO28588). Hitherto, the TRAG was identified as a protein expressed in a TGF-β-resistant cell line; however, its function is unknown (Cytogenet. Cell Genet. 88, 324–325, 2000).

(3) Preparation of an Antibody to Rabconnectin-3β

An expression vector of rabconnectin-3β was constructed using pGex4T-1 (Amersham Biosciences Inc). The construct contained the following amino acid sequences of rabconnectin-3β: pGex4T-1 rabconnectin 3β-1, amino acid numbers 487–625; pGex4T-1 rabconnectin 3β-2, amino acid numbers 615–920.

A GST fusion protein was expressed in *E. coli*, and purified by use of glutathione Sepharose beads (Amersham Biosciences Inc.). A rabbit polyclonal anti-rabconnectin-3β-1 and -2 antibodies were produced by using GST-rabconnectin-3β-1 and -2, respectively, as antigens, and affinity-purified with each antigen covalently coupled to NHS-activated Sepharose beads (Amersham Biosciences Inc.).

(4) Study of Tissue Distribution and Subcellular Distribution of Rabconnectin-3β

The tissue distribution and subcellular distribution of rabconnectin-3β was studied. Regarding the tissue distribution, homogenates of various rat tissues (each 20 μg protein) were subjected to SDS-PAGE, followed by Western blotting with an anti-rabconnectin-3β-2 antibody. Regarding the subcellular distribution, a homogenate of rat cerebra was subjected to subcellular fractionation (J. Biol. Chem., 265, 11872–11879 (1990)), and each fraction (each 10 μg protein) was subjected to SDS-PAGE, followed by Western blotting with an anti-rabconnectin-3β-1 antibody, an anti-rabconnectin-3α antibody, or an anti-Rab3 GEP antibody.

Figure 2:
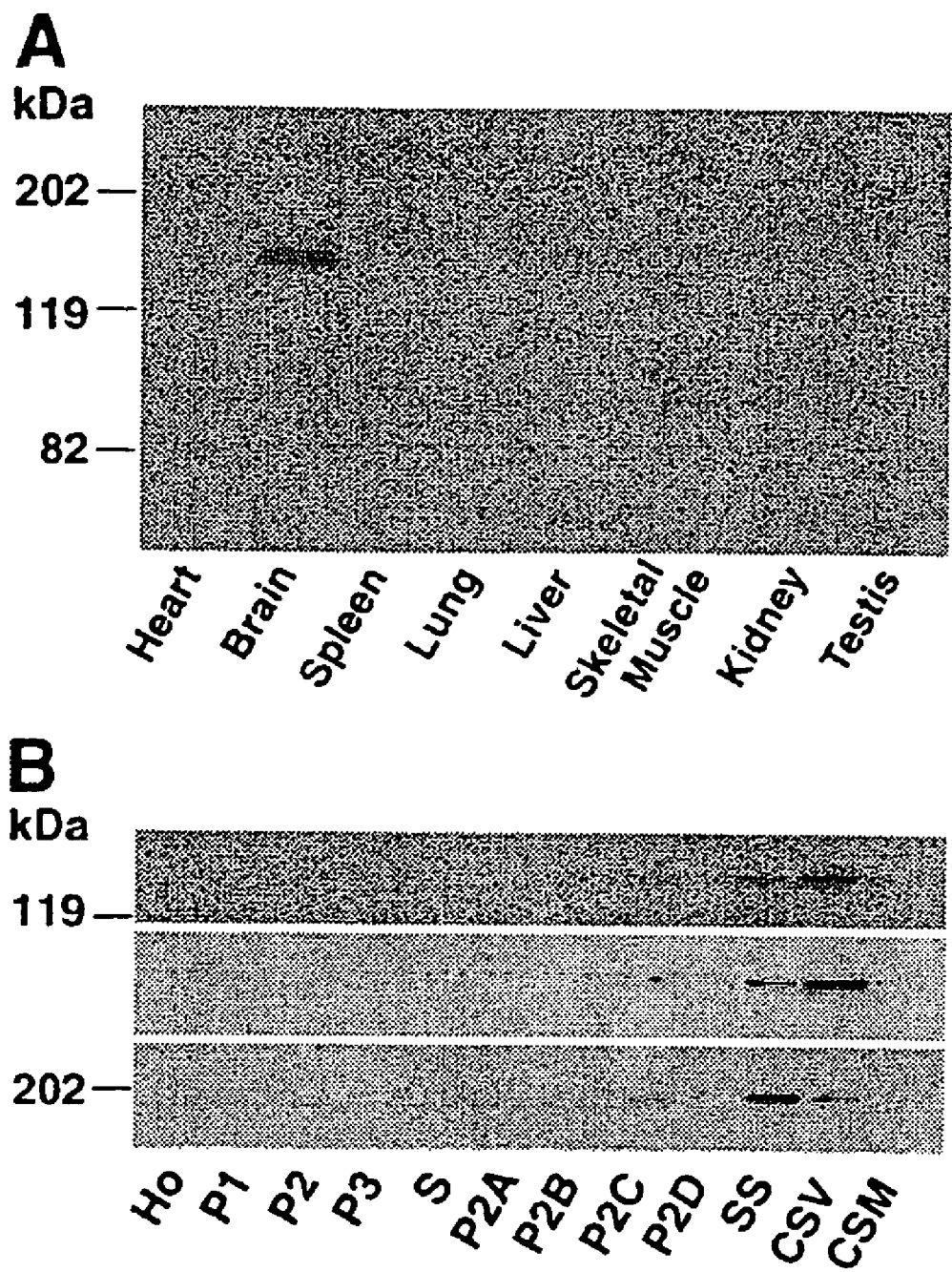
FIG. 2 shows tissue and subcellular distributions of rabconnectin-3β. (A) Tissue distribution of rabconnectin-3β (electrophoresis photograph); and (B) subcellular distribution of rabconnectin-3β (electrophoresis photograph). Rc-3β, rabconnectin-3β; Rc-3α, rabconnectin-3α; GEP, Rab3 GEP; Ho, homogenate fraction; P1, nuclear pellet fraction; P2, crude synaptosome fraction; P3, microsome fraction; S, soluble cytosol fraction; P2A, myelin fraction; P2B, endoplasmic reticulum and Golgi complex fraction; P2C, synaptosome fraction; P2D, mitochondria fraction; SS, synaptic soluble fraction; CSV, crude synaptic vesicle fraction; and CSM, crude synaptic membrane fraction.

As a result, the tissue distribution analysis revealed that the rabconnectin-3β was specifically expressed in the brain (A in FIG. 2). The subcellular distribution analysis in the brain revealed that rabconnectin-3β is highly concentrated in a CSV fraction (B in FIG. 2). The symbols in B of FIG. 2 represent the following fractions and the like: Rc-3β, rabconnectin-3β; Rc-3α, rabconnectin-3α; GEP, Rab3 GEP; Ho, homogenate fraction; P1, nuclear pellet fraction; P2, crude synaptosome fraction; P3, microsome fraction; S, soluble cytosol fraction; P2A, myelin fraction; P2B, endoplasmic reticulum and Golgi complex fraction; P2C, synaptosome fraction; P2D, mitochondria fraction; SS, synaptic soluble fraction; CSV, crude synaptic vesicle fraction; and CSM, crude synaptic membrane fraction. The results shown in the figure are representative of three independent experiments.

Furthermore, regarding a mouse hippocampus and a primary culture of rat hippocampus neurons (J. Biol. Chem., 277, 9629–9632 (2002)), an immunoelectron microscope observation was performed (Biochem. Biophys. Res. Commun., 202, 1235–1243 (1994)).

A sample was doubly stained with an anti-rabconnctin-3α antibody and an anti-rabconnectin-3β-2 antibody, followed by immunofluorescence microscopy.

Figure 3:
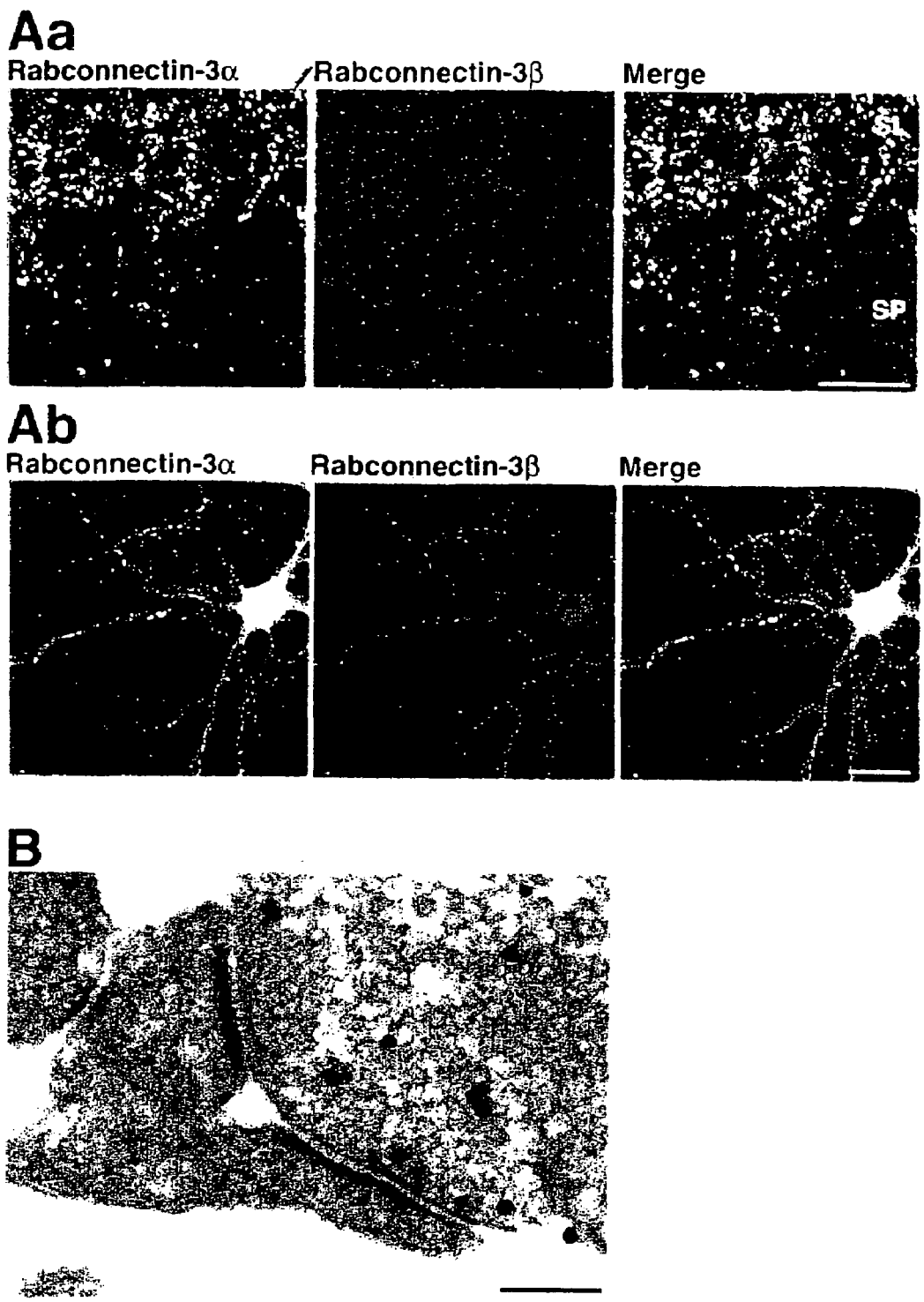
FIG. 3 shows immunofluorescent microscope images (microscope photographs) showing the coexistence of rabconnectin-3α and -3β in synapses.

As a result, it was revealed that rabconnectin-3β is colocalized with rabconnectin-3α in a synapse region of the mouse hippocampus and the primary culture of rat hippocampus neurons (Aa and Ab in FIG. 3). Aa in FIG. 3 represents the mouse hippocampus CA3 region, and Ab represents the rat hippocampus neuron primary culture (20th day of culture). The symbols are as follows: SR, stratum radiatum; SL, stratum lucidum; SP, stratum pyramidale; and a bar, 30 μm.

Furthermore, the neurons on the 22nd day in culture were stained with an anti-rabconnectin-3β-1 antibody (B in FIG. 3). In B of FIG. 3, a bar represents 200 nm. This result showed that rabconnectin-3β is associated with synaptic vesicles (B in FIG. 3).

These results show that rabconnectin-3β and rabconnectin-3α colocalized on synaptic vesicles. The results shown in FIG. 3 are representative of three independent experiments.

(5) Study of Binding of Rabconnectin-3α, Rab3 GEP, and Rab3 GAP to Rabconnectin-3β

Figure 4:
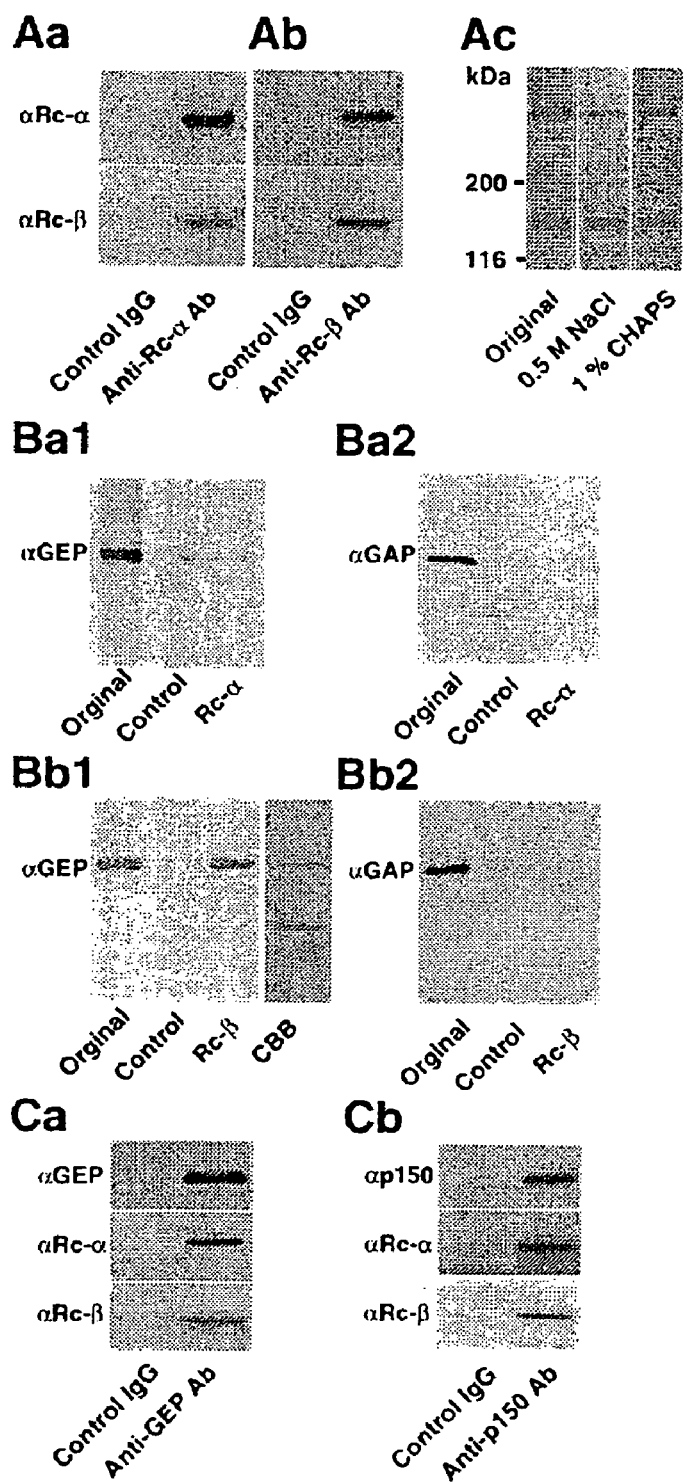
FIG. 4 shows results of Western blotting illustrating the direct binding of Rab3 GEP and indirect binding of Rab3 GAP to rabconnectin-3β (electrophoresis photographs).

The binding of rabconnectin-3β and rabconnectin-3α was studied. An extract of a CSV fraction was immunoprecipitated by an anti-rabconnectin-3α or 3β-2 antibody. Each immunoprecipitate was subjected to SDS-PAGE (8% polyacrylamide gel), followed by Western blotting with the anti-rabconnectin-3α or 3β-1 antibody. Furthermore, the immunoprecipitate by the anti-rabconnectin-3β-2 antibody was first washed with 0.5 M NaCl or 1% CHAPS, and then subjected to SDS-PAGE (8% polyacrylamide gel), followed by protein staining with Coomassie brilliant blue. Aa to Ac in FIG. 4 show the results. Aa is a result of the immunoprecipitate by the anti-rabconnectin-3α antibody; Ab is a result of the immunoprecipitate by the anti-rabconnectin-3β-2 antibody; and Ac is a result of the immunoprecipitate by the anti-rabconnectin-3β-2 antibody with the NaCl or CHAPS treatment.

When rabconnectin-3α was immunoprecipitated by its antibody from the extract of the P2C fraction, rabconnectin-3β was coimmunoprecipitated as expected from Western blotting (Aa in FIG. 4). Conversely, when rabconnectin-3β was immunoprecipitated by its antibody from the extract of the P2C fraction, rabconnectin-3α was coimmunoprecipitated (Ab in FIG. 4). Rabconnectin-3α and rabconnectin-3β coimmunoprecipitated using the anti-rabconnectin-3β-2 antibody were washed with either 0.5 M NaCl or 1% CHAPS, and subjected to protein staining with Coomassie brilliant blue. Both the proteins were not dissociated from each other, and stained in an apparently similar molecular ratio (Ac in FIG. 4). Rabconnectin-3α and rabconnectin-3β were dissociated partly with 1 M NaCl and completely with 1% deoxycholate (data not shown). These results indicate that rabconnectin-3α and rabconnectin-3β form a complex.

Next, it was examined which protein, rabconnectin-3α or 3α bound Rab3 GEP and Rab3 GAP. For this purpose, pure samples of rabconnectin-3β and Rab3 GEP from insect cells and non-catalystic subunits of Rab3 GAP (p150) from *E. coli* were prepared (see J. Biol. Chem., 272, 3875–3878 (1997), J. Biol. Chem., 273, 24781–24785). As rabconnetin-3α is a huge protein, its full-length protein has not been expressed in a mammalian cell line such as COS7 cells, and its pure recombinant sample has not been prepared from *E. coli* or insect cells. Therefore, native rabconnectin-3α, and a complex of rabconnectin-3α and -3β were prepared from the P2C fraction of rat brain. The complex of rabconnectin- 3α and -3β was immunoprecipitated from a P2C fraction, by an anti-rabconnectin-3β-2 antibody bound to protein A Sepharose beads, followed by washing the beads with 0.5 M NaCl. This sample was used as the complex of rabconnectin-3α and -3β. In another experiment for preparing a chain, the complex of rabconnectin-3α and -3β immunoprecipitated from the P2C fraction by the anti-rabconnecti-3β-2 antibody bound to the protein A Sepharose beads was washed with 1 M NaCl to dissociate rabconnectin-3α from rabconnectin-3β. Rabconnectin-3α dissociated from the beads was immunoprecipitated by an anti-rabconnectin-3α antibody immobilized to the protein A Sepharose beads.

Affinity beads coupled with rabconnectin-3β, -3α, or a complex thereof were prepared. For the rabconnectin-3β-coupled beads, a baculovirus bearing a rabconnectin-3β cDNA was prepared with pFastBac HTa rabconnectin-3β according to a manufacturer's protocol (GIBCO BRL), High Five cells (Invitrogen) were transfected with the baculovirus. The extract of cells (5 mg protein) was prepared with Buffer A, and incubated overnight at 4° C. with an anti-rabconnectin-3β-2 antibody immobilized on protein A Sepharose beads (20 μl wet volume). For the rabconnectin-3α-coupled beads, a complex of rabconectin-3α and -3β was first immunoprecipitated from the above P2C fraction, by the anti-rabconnectin-3β-2 antibody coupled with the protein A Sepharose beads. Rabconectin-3α was then dissociated from the beads by washing at 4° C. for one hour with Buffer A containing 1 M NaCl. The dissociated rabconnectin-3α (0.4 μg protein) was collected, and incubated at 4° C. overnight with the anti-rabconnectin-3α antibody immobilized on the protein A Sepharose beads (20 μl wet volume). For the complex-coupled beads, a complex of rabconnectin-3α and -3β was similarly immunoprecipitated from the P2C fraction, followed by washing the beads with Buffer A containing 0.5 M NaCl. The affinity beads coupled with rabconnectin 3α, 3β, or a complex thereof were washed extensively with Buffer A.

Recombinant Rab3 GEP or GAP p150 was incubated with the protein A Sepharose beads coupled with recombinant rabconnectin 3β or native rabconnectin-3α. On the other hand, after rabconnectin-3α and -3β were immunoprecipitated from the P2C fraction, by the anti-rabconnectin-3β-2 antibody immobilized on the beads, followed by washing the beads with 0.5 M NaCl, Rab3 GEP or GAP p150 was incubated with the beads. After the incubation, they were subjected to SDS-PAGE (8% polyacrylamide gel), followed by protein staining with Coomassie brilliant blue or Western blotting with anti-Rab3 GEP or GAP p150 antibody. Ba1 to Bb2 in FIG. 4 show the results. Ba shows rabconnectin-3α-coupled beads, Bb shows rabconnectin-3β-coupled beads, 1 represents Rab3 GEP, and 2 represents Rab3 GAP p150.

As a result, rabconnectin-3β bound recombinant Rab3 GEP stoichiometrically, whereas rabconectin-3α did not (Ba1 and Bb1 in FIG. 4). The complex directly bound Rab3 GEP; but stoichiometry of this binding was much less than that of rabconnectin-3β (data now shown). On the other hand, none of rabconnectin-3α, -3β, and a complex thereof bound Rab3 GAP (Ba2, Bb2 in FIG. 4 (data regarding a complex are not shown)).

The extract of the CSV fraction was immunoprecipitated by an anti-Rab3 GEP or GAP p150 antibody. Each immunoprecipitate was subjected to SDS-PAGE (8% polyacrylamide gel), followed by Western blotting with anti-Rab3 GEP or GAP p150 antibody and anti-rabconnectin-3α antibody and an anti-rabconnectin-3β-1 antibody. Ca and Cb in FIG. 4 show the results. Ca represents the result of an immunoprecipitate by the anti-Rab3 GEP antibody, and Cb represents the result of an immunoprecipitate by the anti-Rab3 GAP p150 antibody.

Consistently, rabconnectin-3β was coimmunoprecipitated from the extract of the P2C fraction, with Rab3 GEP or Rab3 GAP p150, by an anti-Rab3 GEP or anti-Rab3 GAP p150 antibody, in the same way as in rabconnectin-3α. (see Ca and Cb in FIG. 4, and A in FIG. 1)

Taken together, the above-mentioned results indicate that rabconnectin-3β directly binds Rab3 GEP, and indirectly binds Rab3 GAP through an unidentified molecule under regulated manners. The results in FIG. 4 are representative of three independent experiments.

The anti-Rab3 GAP p150 antibody, the anti-Rab3 GEP antibody, and the anti-rabconnectin-3α antibody used in Example 1 are a mouse monoclonal anti-Rab3 GAP p150 antibody, a rabbit polyclonal anti-Rab3 GEP antibody, and a rat polyclonal anti-rabconnectin-3α antibody, prepared by methods described in J. Biol. Chem., 277, 9629–9632 (2002), J. Biol. Chem., 273, 24781–24785 (1998), and J. Biol. Chem., 273, 34580–34585 (1998). J. Biol. Chem., 277, 9629–9632 (2002) shows that rabconnectin-3α is coimmunoprecipitated from the CSV fraction with Rab3 GEP or GAP by an anti-Rab3 GEP antibody or a Rab3 GAP p150 antibody, respectively.

Example 2

Neuroblastoma cells PC-12 (1×10$^6$) were cultured in a well coated with poly-L-lysine. On the following day of the culture starting day, pCMV myc expressing myc and pCMV myc:p160 expressing P160 (rabconnectin-3β) as a fusion protein with myc were transfected to the cells by a lipofectin method. pCMV myc is described in J. Biol. Chem, 272, 11943–11951 (1997). pCMV myc:p160 integrates a DNA encoding an amino acid numbers 1 to 1490 (full length) of rabconnectin-3β so that a fusion protein of rabconnectin-3β and myc is expressed.

Two days after the transfection, a low-potassium (potassium concentration: 4.7 mM) buffer was added to the wells, followed by incubation at 37° C. for 10 minutes. Then, the buffer was removed, and a low-potassium or high-potassium (potassium concentration: 60 mM) buffer was added to the wells, followed by incubation at 37° C. for 10 minutes. Thereafter, the amounts of growth hormones (GH) secreted to the supernatant and GH remaining in the cells were measured by a hGH ELISA kit (Roche Co.). The results were represented as a ratio (%) of secreted GH, with the total amount of GH in the supernatant and the cells being 100%.

Consequently, the growth hormones were released only in an amount of 2.3% of the total amount with the low-potassium buffer, whereas the growth hormones were released in an amount of 8.9% of the total amount with the high-potassium buffer. The release of the growth hormones increased by the stimulation of potassium was suppressed to 7.0% by the expression of p160. From these results, it is considered that p160 participates in the regulation of the transportation of synaptic vesicles such as the release of the growth hormones.

The invention claimed is:

1. A method of screening for a material that promotes or inhibits binding between a rabconnectin-3-binding protein and rabconnectin-3, comprising the steps of:
   contacting a rabconnectin-3-binding protein with rabconnectin-3 in the presence and absence of a candidate material, and
   determining whether the candidate material increases or decreases binding between the rabconnectin-3-binding protein and rabconnectin-3, wherein the rabconnectin-3-binding protein is a protein comprising the amino acid sequence of SEQ ID NO: 2.

2. The method of claim 1, wherein the amino acid sequence of the rabconnectin-3-binding protein consists of the amino acid sequence of SEQ ID NO: 2.

3. A method of screening for a material that promotes or inhibits binding between a rabconnectin-3-binding protein and rabconnectin-3, comprising the steps of: contacting a rabconnectin-3-binding protein with rabconnectin-3 in the presence and absence of a candidate material, and
   determining whether the candidate material increases or decreases binding between the rabconnectin-3-binding protein and rabconnectin-3, wherein the rabconnectin-3-binding protein is a protein comprising the amino acid sequence of SEQ ID NO: 2 with one to thirty amino acids deleted, replaced, or added, and having an activity of binding rabconnectin-3 and a GDP/GTP exchange protein.

4. The method of claim 3, wherein the rabconnectin-3-binding protein is obtained by subjecting the DNA encoding the protein comprising the amino acid sequence of SEQ ID NO: 2 to mutagenesis and selecting for a DNA encoding a mutant protein having an activity of binding rabconnectin-3 and a GDP/GTP exchange protein.

* * * * *

SEQUENCE LISTING

<160> NUMBER OF SEQ ID NOS: 4

<210> SEQ ID NO 1
<211> LENGTH: 4473
<212> TYPE: DNA
<213> ORGANISM: Homo sapiens
<220> FEATURE:
<221> NAME/KEY: CDS
<222> LOCATION: (1)..(4470)

<400> SEQUENCE: 1

```
atg gca gga aac agc ctt gtt cta ccc att gtt ctt tgg ggt cga aaa       48
Met Ala Gly Asn Ser Leu Val Leu Pro Ile Val Leu Trp Gly Arg Lys
1               5                   10                  15 gcg ccc aca cat tgc atc tca gcg gta ctt tta aca gat gat ggg gcc       96
Ala Pro Thr His Cys Ile Ser Ala Val Leu Leu Thr Asp Asp Gly Ala
                20                  25                  30 acg atc gta aca gga tgt cac gac gga caa ata tgt ctc tgg gat ctt      144
Thr Ile Val Thr Gly Cys His Asp Gly Gln Ile Cys Leu Trp Asp Leu
            35                  40                  45 tca gta gaa ctg caa att aat cct cga gca ctg ttg ttt ggt cat aca      192
Ser Val Glu Leu Gln Ile Asn Pro Arg Ala Leu Leu Phe Gly His Thr
        50                  55                  60 gca tca atc act tgt ttg tct aaa gct tgt gct tcc agt gac aaa cag      240
Ala Ser Ile Thr Cys Leu Ser Lys Ala Cys Ala Ser Ser Asp Lys Gln
65                  70                  75                  80 tat att gtg agt gca tct gaa agt gga gag atg tgc ctc tgg gat gtg      288
Tyr Ile Val Ser Ala Ser Glu Ser Gly Glu Met Cys Leu Trp Asp Val
                85                  90                  95 agt gat ggc aga tgt att gaa ttt aca aaa tta gct tgc aca cat act      336
Ser Asp Gly Arg Cys Ile Glu Phe Thr Lys Leu Ala Cys Thr His Thr
                100                 105                 110 ggc ata cag ttc tac cag ttc tct gtt ggg aat cag cga gaa gga agg      384
Gly Ile Gln Phe Tyr Gln Phe Ser Val Gly Asn Gln Arg Glu Gly Arg
            115                 120                 125 ctt tta tgc cac gga cat tac cct gaa atc ctt gtt gtg gat gct acc      432
Leu Leu Cys His Gly His Tyr Pro Glu Ile Leu Val Val Asp Ala Thr
        130                 135                 140 agc ctt gaa gta tta tac tcc tta gta tca aag ata tca cca gac tgg      480
Ser Leu Glu Val Leu Tyr Ser Leu Val Ser Lys Ile Ser Pro Asp Trp
145                 150                 155                 160 att agc tcc atg agt att att cga tcc cac cga aca caa gag gac aca      528
Ile Ser Ser Met Ser Ile Ile Arg Ser His Arg Thr Gln Glu Asp Thr
                165                 170                 175 gtg gta gca ctc tcg gtg act ggc atc ctg aag gtc tgg att gtt acc      576
Val Val Ala Leu Ser Val Thr Gly Ile Leu Lys Val Trp Ile Val Thr
                180                 185                 190 tcg gaa ata agt gac atg cag gat act gag cca ata ttt gag gag gaa      624
Ser Glu Ile Ser Asp Met Gln Asp Thr Glu Pro Ile Phe Glu Glu Glu
            195                 200                 205 tcc aaa cca att tat tgt cag aat tgc caa agc atc tct ttt tgt gca      672
Ser Lys Pro Ile Tyr Cys Gln Asn Cys Gln Ser Ile Ser Phe Cys Ala
        210                 215                 220 ttt aca caa agg tca ctt ttg gtt gtg tgt tcc aaa tat tgg agg gtg      720
Phe Thr Gln Arg Ser Leu Leu Val Val Cys Ser Lys Tyr Trp Arg Val
225                 230                 235                 240 ttc gat gcc gga gac tat tcc ttg ttg tgt tca ggt cct agt gaa aat      768
Phe Asp Ala Gly Asp Tyr Ser Leu Leu Cys Ser Gly Pro Ser Glu Asn
                245                 250                 255
```

-continued

| | |
|---|---|
| gga cag aca tgg acc ggg ggg gac ttt gtc tca tca gat aaa gtc atc<br>Gly Gln Thr Trp Thr Gly Gly Asp Phe Val Ser Ser Asp Lys Val Ile<br>260                         265                      270 | 816 |
| att tgg aca gaa aat ggg caa agt tat att tac aaa cta cct gcc agt<br>Ile Trp Thr Glu Asn Gly Gln Ser Tyr Ile Tyr Lys Leu Pro Ala Ser<br>275                         280                      285 | 864 |
| tgc ctt cca gct agt gat tca ttc cgc agt gat gtg ggg aag gca gtt<br>Cys Leu Pro Ala Ser Asp Ser Phe Arg Ser Asp Val Gly Lys Ala Val<br>290                         295                      300 | 912 |
| gaa aat tta att cct cct gta caa cat atc ctc ttg gat cga aaa gat<br>Glu Asn Leu Ile Pro Pro Val Gln His Ile Leu Leu Asp Arg Lys Asp<br>305                       310                     315                320 | 960 |
| aaa gag ttg cta att tgt cct cct gtt act cgg ttc ttc tat gga tgc<br>Lys Glu Leu Leu Ile Cys Pro Pro Val Thr Arg Phe Phe Tyr Gly Cys<br>                  325                     330                     335 | 1008 |
| aga gaa tat ttc cat aaa ctg tta att cag ggt gat tct tct gga agg<br>Arg Glu Tyr Phe His Lys Leu Leu Ile Gln Gly Asp Ser Ser Gly Arg<br>                  340                     345                     350 | 1056 |
| ttg aat att tgg aac ata tca gac aca gct gat aaa cag gga agt gaa<br>Leu Asn Ile Trp Asn Ile Ser Asp Thr Ala Asp Lys Gln Gly Ser Glu<br>                  355                     360                     365 | 1104 |
| gaa ggg ctg gca atg aca act tct att agt ttg caa gag gca ttt gat<br>Glu Gly Leu Ala Met Thr Thr Ser Ile Ser Leu Gln Glu Ala Phe Asp<br>370                         375                      380 | 1152 |
| aaa ctg aat cct tgt cct gct gga att ata gat cag ctg agt gtg att<br>Lys Leu Asn Pro Cys Pro Ala Gly Ile Ile Asp Gln Leu Ser Val Ile<br>385                       390                     395                  400 | 1200 |
| ccc aat agt aat gaa cct ctt aaa gta act gca agt gtg tac ata cca<br>Pro Asn Ser Asn Glu Pro Leu Lys Val Thr Ala Ser Val Tyr Ile Pro<br>                  405                     410                     415 | 1248 |
| gca cat gga cga ctt gtt tgt ggt cgt gaa gat gga agc ata gtt att<br>Ala His Gly Arg Leu Val Cys Gly Arg Glu Asp Gly Ser Ile Val Ile<br>                  420                     425                     430 | 1296 |
| gta cct gcc aca cag acg gcc ata gta cag ctg ttg caa ggg gaa cac<br>Val Pro Ala Thr Gln Thr Ala Ile Val Gln Leu Leu Gln Gly Glu His<br>                  435                     440                     445 | 1344 |
| atg ctc aga aga ggt tgg cca cct cac aga aca ctc cgt ggt cat cgg<br>Met Leu Arg Arg Gly Trp Pro Pro His Arg Thr Leu Arg Gly His Arg<br>450                         455                      460 | 1392 |
| aac aaa gtc aca tgt ttg cta tat cct cat cag gtc tca gct cgg tat<br>Asn Lys Val Thr Cys Leu Leu Tyr Pro His Gln Val Ser Ala Arg Tyr<br>465                       470                     475                  480 | 1440 |
| gat caa aga tac ctg ata tct gga ggt gtg gat ttt tca gtc ata att<br>Asp Gln Arg Tyr Leu Ile Ser Gly Gly Val Asp Phe Ser Val Ile Ile<br>                  485                     490                     495 | 1488 |
| tgg gac ata ttt tct gga gaa atg aaa cat atc ttc tgt gtt cat ggt<br>Trp Asp Ile Phe Ser Gly Glu Met Lys His Ile Phe Cys Val His Gly<br>                  500                     505                     510 | 1536 |
| ggt gag att act caa ctt cta gtt cca cct gaa aac tgt agt gca aga<br>Gly Glu Ile Thr Gln Leu Leu Val Pro Pro Glu Asn Cys Ser Ala Arg<br>                  515                     520                     525 | 1584 |
| gta cag cac tgc atc tgc tct gta gcc agt gac cac tca gta gga ctt<br>Val Gln His Cys Ile Cys Ser Val Ala Ser Asp His Ser Val Gly Leu<br>530                         535                      540 | 1632 |
| cta agt ttg cga gag aaa aaa tgc ata atg ttg gca tct cgt cac ctt<br>Leu Ser Leu Arg Glu Lys Lys Cys Ile Met Leu Ala Ser Arg His Leu<br>545                       550                     555                560 | 1680 |
| ttt cct att caa gta atc aaa tgg agg cct tct gat gat tac ctg gtg<br>Phe Pro Ile Gln Val Ile Lys Trp Arg Pro Ser Asp Asp Tyr Leu Val<br>                  565                     570                     575 | 1728 |

| | |
|---|---|
| gtg ggg tgt tca gat ggt tct gtg tac gtc tgg caa atg gat act ggt<br>Val Gly Cys Ser Asp Gly Ser Val Tyr Val Trp Gln Met Asp Thr Gly<br>580 585 590 | 1776 |
| gca ttg gat cgt tgt gtg atg ggg ata aca gca gtt gag att cta aac<br>Ala Leu Asp Arg Cys Val Met Gly Ile Thr Ala Val Glu Ile Leu Asn<br>595 600 605 | 1824 |
| gct tgt gat gaa gct gtt cct gct gct gtt gat tca ctt agt cat cca<br>Ala Cys Asp Glu Ala Val Pro Ala Ala Val Asp Ser Leu Ser His Pro<br>610 615 620 | 1872 |
| gca gtc aac cta aaa caa gct atg acg aga cgt agt ctt gct gct ctt<br>Ala Val Asn Leu Lys Gln Ala Met Thr Arg Arg Ser Leu Ala Ala Leu<br>625 630 635 640 | 1920 |
| aaa aat atg gcc cat cat aag cta caa acc ctt gca act aac ctc ttg<br>Lys Asn Met Ala His His Lys Leu Gln Thr Leu Ala Thr Asn Leu Leu<br>645 650 655 | 1968 |
| gct tct gag gca tct gac aag gga aat tta cct aaa tat tct cat aac<br>Ala Ser Glu Ala Ser Asp Lys Gly Asn Leu Pro Lys Tyr Ser His Asn<br>660 665 670 | 2016 |
| tcc ctg atg gtt caa gca ata aag aca aac cta aca gac ccg gac ata<br>Ser Leu Met Val Gln Ala Ile Lys Thr Asn Leu Thr Asp Pro Asp Ile<br>675 680 685 | 2064 |
| cat gtg cta ttc ttt gat gtg gaa gcg ttg att att caa ctc ctg act<br>His Val Leu Phe Phe Asp Val Glu Ala Leu Ile Ile Gln Leu Leu Thr<br>690 695 700 | 2112 |
| gaa gaa gcc tct agg ccg aat act gct ctt att tcc cca gag aat ttg<br>Glu Glu Ala Ser Arg Pro Asn Thr Ala Leu Ile Ser Pro Glu Asn Leu<br>705 710 715 720 | 2160 |
| caa aaa gca tct ggc agt tca gac aaa ggg ggc tct ttt tta act gga<br>Gln Lys Ala Ser Gly Ser Ser Asp Lys Gly Gly Ser Phe Leu Thr Gly<br>725 730 735 | 2208 |
| aaa cga gca gca gtt ctc ttc caa caa gtg aaa gaa acg atc aaa gag<br>Lys Arg Ala Ala Val Leu Phe Gln Gln Val Lys Glu Thr Ile Lys Glu<br>740 745 750 | 2256 |
| aac atc aag gaa cac ctc ctt gat gat gaa gag gag gat gag gag ata<br>Asn Ile Lys Glu His Leu Leu Asp Asp Glu Glu Glu Asp Glu Glu Ile<br>755 760 765 | 2304 |
| atg agg cag aga agg gaa gaa agt gat cct gaa tat cgg tcc agc aaa<br>Met Arg Gln Arg Arg Glu Glu Ser Asp Pro Glu Tyr Arg Ser Ser Lys<br>770 775 780 | 2352 |
| tca aag cca ttg acc cta tta gaa tat aat tta act atg gac act gca<br>Ser Lys Pro Leu Thr Leu Leu Glu Tyr Asn Leu Thr Met Asp Thr Ala<br>785 790 795 800 | 2400 |
| aag ctg ttt atg tcc tgc ctt cac gcc tgg ggt ttg aat gaa gta ctg<br>Lys Leu Phe Met Ser Cys Leu His Ala Trp Gly Leu Asn Glu Val Leu<br>805 810 815 | 2448 |
| gat gaa gtt tgc ctg gat cgc ctt gga atg ctg aaa ccc cac tgc acc<br>Asp Glu Val Cys Leu Asp Arg Leu Gly Met Leu Lys Pro His Cys Thr<br>820 825 830 | 2496 |
| gta tcg ttt ggc ctc ttg tca aga gga ggc cat atg tca ctg atg ctg<br>Val Ser Phe Gly Leu Leu Ser Arg Gly Gly His Met Ser Leu Met Leu<br>835 840 845 | 2544 |
| ccg ggt tat aat cag cct gct tgt aaa ctg tca cat ggg aaa aca gaa<br>Pro Gly Tyr Asn Gln Pro Ala Cys Lys Leu Ser His Gly Lys Thr Glu<br>850 855 860 | 2592 |
| gta gga agg aag ctg cca gcg tct gag gga gta gga aag gga act tac<br>Val Gly Arg Lys Leu Pro Ala Ser Glu Gly Val Gly Lys Gly Thr Tyr<br>865 870 875 880 | 2640 |
| gga gtg tcc cgt gcc gtc acc aca cag cat ctc ctg tct atc att tct<br>Gly Val Ser Arg Ala Val Thr Thr Gln His Leu Leu Ser Ile Ile Ser | 2688 |

-continued

```
                       885                 890                 895
ttg gca aat act tta atg agt atg acc aat gca act ttt att ggt gat      2736
Leu Ala Asn Thr Leu Met Ser Met Thr Asn Ala Thr Phe Ile Gly Asp
                900                 905                 910 cat atg aag aag ggt cct acc agg cca cct aga cca agc acc cca gac      2784
His Met Lys Lys Gly Pro Thr Arg Pro Pro Arg Pro Ser Thr Pro Asp
            915                 920                 925 ctt tct aag gca agg ggt tcc cct cca act tcc agt aat att gtg caa      2832
Leu Ser Lys Ala Arg Gly Ser Pro Pro Thr Ser Ser Asn Ile Val Gln
        930                 935                 940 gga cag att aaa caa gtt gct gca cct gtc gtt tcc gct cgg tct gat      2880
Gly Gln Ile Lys Gln Val Ala Ala Pro Val Val Ser Ala Arg Ser Asp
945                 950                 955                 960 gct gat cac tct ggc tct gac cct cct tct gct cct gct tta cat acc      2928
Ala Asp His Ser Gly Ser Asp Pro Pro Ser Ala Pro Ala Leu His Thr
                965                 970                 975 tgt ttc tta gta aat gaa ggt tgg agt cag tta gct gct atg cac tgt      2976
Cys Phe Leu Val Asn Glu Gly Trp Ser Gln Leu Ala Ala Met His Cys
            980                 985                 990 gtt atg ctg cca gac cta ctg gga ttg gat aaa ttt agg cct ccc ctt      3024
Val Met Leu Pro Asp Leu Leu Gly Leu Asp Lys Phe Arg Pro Pro Leu
        995                 1000                1005 ctg gag atg ctg gcc cga aga tgg caa gat cga tgc ttg gag gtg          3069
Leu Glu Met Leu Ala Arg Arg Trp Gln Asp Arg Cys Leu Glu Val
    1010                1015                1020 aga gaa gcc gca cag gcc ctg ctt ctg gcg gaa ctg aga aga att          3114
Arg Glu Ala Ala Gln Ala Leu Leu Leu Ala Glu Leu Arg Arg Ile
    1025                1030                1035 gag cag gca ggc agg aag gaa gcc att gat gcc tgg gct cct tac          3159
Glu Gln Ala Gly Arg Lys Glu Ala Ile Asp Ala Trp Ala Pro Tyr
    1040                1045                1050 tta cct cag tac ata gac cac gtc ata tca cct gga gtc aca tca          3204
Leu Pro Gln Tyr Ile Asp His Val Ile Ser Pro Gly Val Thr Ser
    1055                1060                1065 gaa gcc gcg cag act atc acc acg gct cct gat gcc tca ggg cct          3249
Glu Ala Ala Gln Thr Ile Thr Thr Ala Pro Asp Ala Ser Gly Pro
    1070                1075                1080 gaa gca aaa gtc cag gag gaa gag cat gac ctt gtt gac gat gac          3294
Glu Ala Lys Val Gln Glu Glu Glu His Asp Leu Val Asp Asp Asp
    1085                1090                1095 atc acc act ggt tgc tta tca agt gtc cca caa atg aaa aaa att          3339
Ile Thr Thr Gly Cys Leu Ser Ser Val Pro Gln Met Lys Lys Ile
    1100                1105                1110 tct aca tct tac gag gaa aga cgg aag caa gct acc gct att gtt          3384
Ser Thr Ser Tyr Glu Glu Arg Arg Lys Gln Ala Thr Ala Ile Val
    1115                1120                1125 tta ctt gga gta ata gga gct gaa ttt ggt gct gaa att gaa cct          3429
Leu Leu Gly Val Ile Gly Ala Glu Phe Gly Ala Glu Ile Glu Pro
    1130                1135                1140 cct aaa cta ttg acc aga cct cga agc tct agc caa att cct gag          3474
Pro Lys Leu Leu Thr Arg Pro Arg Ser Ser Ser Gln Ile Pro Glu
    1145                1150                1155 gga ttc ggg ttg act agt ggt gga tcc aac tac tcg ctg gcc aga          3519
Gly Phe Gly Leu Thr Ser Gly Gly Ser Asn Tyr Ser Leu Ala Arg
    1160                1165                1170 cat act tgc aag gca ctg acg ttt ctt ctg cta cag cct cca agc          3564
His Thr Cys Lys Ala Leu Thr Phe Leu Leu Leu Gln Pro Pro Ser
    1175                1180                1185 ccc aaa ctt cct cca cac agc act atc cga aga aca gcc att gat          3609
```

-continued

|     |     |     |     |     |     |     |     |     |     |     |     |      |
|-----|-----|-----|-----|-----|-----|-----|-----|-----|-----|-----|-----|------|
| Pro | Lys | Leu | Pro | Pro | His | Ser | Thr | Ile | Arg | Arg | Thr | Ala Ile Asp |
|     | 1190|     |     |     | 1195|     |     |     | 1200|     |     |      | ctg att gga cgt ggg ttc act gtt tgg gag cct tac atg gat gtg  3654
Leu Ile Gly Arg Gly Phe Thr Val Trp Glu Pro Tyr Met Asp Val
    1205            1210            1215 tcc gct gtt ctg atg ggg ctt ctc gaa ctt tgt gcc gat gcc gag  3699
Ser Ala Val Leu Met Gly Leu Leu Glu Leu Cys Ala Asp Ala Glu
    1220            1225            1230 aaa caa ctt gcc aac atc aca atg ggg ttg cct ctg agc cca gca  3744
Lys Gln Leu Ala Asn Ile Thr Met Gly Leu Pro Leu Ser Pro Ala
    1235            1240            1245 gct gac tcg gcc cgc tct gcg agg cat gcc ctc tcg ctc att gcc  3789
Ala Asp Ser Ala Arg Ser Ala Arg His Ala Leu Ser Leu Ile Ala
    1250            1255            1260 acc gcc aga cca ccc gcc ttc atc acc acc ata gcc aaa gag gta  3834
Thr Ala Arg Pro Pro Ala Phe Ile Thr Thr Ile Ala Lys Glu Val
    1265            1270            1275 cac aga cat acg gct ctt gca gca aat acc caa tca cag cag aat  3879
His Arg His Thr Ala Leu Ala Ala Asn Thr Gln Ser Gln Gln Asn
    1280            1285            1290 atg cac aca aca act ctt gca cga gct aaa ggg gaa att ttg aga  3924
Met His Thr Thr Thr Leu Ala Arg Ala Lys Gly Glu Ile Leu Arg
    1295            1300            1305 gtc att gaa att ctt att gaa aag atg ccc aca gat gtt gtg gat  3969
Val Ile Glu Ile Leu Ile Glu Lys Met Pro Thr Asp Val Val Asp
    1310            1315            1320 ctt ctc gtg gag gtt atg gac atc att atg tac tgc ctt gaa gga  4014
Leu Leu Val Glu Val Met Asp Ile Ile Met Tyr Cys Leu Glu Gly
    1325            1330            1335 tct tta gtt aaa aag aaa ggt ctt caa gaa tgt ttc cca gcc atc  4059
Ser Leu Val Lys Lys Lys Gly Leu Gln Glu Cys Phe Pro Ala Ile
    1340            1345            1350 tgc agg ttc tac atg gtc agc tat tat gag cgg aat cac aga ata  4104
Cys Arg Phe Tyr Met Val Ser Tyr Tyr Glu Arg Asn His Arg Ile
    1355            1360            1365 gca gtt gga gct cgc cat ggt tca gtg gcc ctg tac gac atc cgg  4149
Ala Val Gly Ala Arg His Gly Ser Val Ala Leu Tyr Asp Ile Arg
    1370            1375            1380 act gga aaa tgt cag aca atc cat gga cac aag gga cca atc act  4194
Thr Gly Lys Cys Gln Thr Ile His Gly His Lys Gly Pro Ile Thr
    1385            1390            1395 gca gtg gct ttt gct cct gat gga aga tat ctt gcc acc tac tca  4239
Ala Val Ala Phe Ala Pro Asp Gly Arg Tyr Leu Ala Thr Tyr Ser
    1400            1405            1410 aac act gac agc cac att tct ttt tgg cag atg aac acg tca ctg  4284
Asn Thr Asp Ser His Ile Ser Phe Trp Gln Met Asn Thr Ser Leu
    1415            1420            1425 ctg gga agc atc ggc atg ctg aac tcg gca cct cag ctg cgc tgc  4329
Leu Gly Ser Ile Gly Met Leu Asn Ser Ala Pro Gln Leu Arg Cys
    1430            1435            1440 att aaa acc tac cag gtg ccc cct gtg cag ccc gcg tcc ccc ggc  4374
Ile Lys Thr Tyr Gln Val Pro Pro Val Gln Pro Ala Ser Pro Gly
    1445            1450            1455 tcc cac aat gcc ctc aag ctg gcc cgg ctc atc tgg act tcc aac  4419
Ser His Asn Ala Leu Lys Leu Ala Arg Leu Ile Trp Thr Ser Asn
    1460            1465            1470 cgc aac gtc atc ctc atg gcc cat gac ggg aag gag cac cgc ttc  4464
Arg Asn Val Ile Leu Met Ala His Asp Gly Lys Glu His Arg Phe
    1475            1480            1485

```
atg gtc taa                                                              4473
Met Val
    1490
```

<210> SEQ ID NO 2
<211> LENGTH: 1490
<212> TYPE: PRT
<213> ORGANISM: Homo sapiens

<400> SEQUENCE: 2

```
Met Ala Gly Asn Ser Leu Val Leu Pro Ile Val Leu Trp Gly Arg Lys
1               5                   10                  15

Ala Pro Thr His Cys Ile Ser Ala Val Leu Leu Thr Asp Asp Gly Ala
            20                  25                  30

Thr Ile Val Thr Gly Cys His Asp Gly Gln Ile Cys Leu Trp Asp Leu
        35                  40                  45

Ser Val Glu Leu Gln Ile Asn Pro Arg Ala Leu Leu Phe Gly His Thr
    50                  55                  60

Ala Ser Ile Thr Cys Leu Ser Lys Ala Cys Ala Ser Ser Asp Lys Gln
65                  70                  75                  80

Tyr Ile Val Ser Ala Ser Glu Ser Gly Glu Met Cys Leu Trp Asp Val
                85                  90                  95

Ser Asp Gly Arg Cys Ile Glu Phe Thr Lys Leu Ala Cys Thr His Thr
            100                 105                 110

Gly Ile Gln Phe Tyr Gln Phe Ser Val Gly Asn Gln Arg Glu Gly Arg
        115                 120                 125

Leu Leu Cys His Gly His Tyr Pro Glu Ile Leu Val Val Asp Ala Thr
    130                 135                 140

Ser Leu Glu Val Leu Tyr Ser Leu Val Ser Lys Ile Ser Pro Asp Trp
145                 150                 155                 160

Ile Ser Ser Met Ser Ile Ile Arg Ser His Arg Thr Gln Glu Asp Thr
                165                 170                 175

Val Val Ala Leu Ser Val Thr Gly Ile Leu Lys Val Trp Ile Val Thr
            180                 185                 190

Ser Glu Ile Ser Asp Met Gln Asp Thr Glu Pro Ile Phe Glu Glu Glu
        195                 200                 205

Ser Lys Pro Ile Tyr Cys Gln Asn Cys Gln Ser Ile Ser Phe Cys Ala
    210                 215                 220

Phe Thr Gln Arg Ser Leu Leu Val Val Cys Ser Lys Tyr Trp Arg Val
225                 230                 235                 240

Phe Asp Ala Gly Asp Tyr Ser Leu Leu Cys Ser Gly Pro Ser Glu Asn
                245                 250                 255

Gly Gln Thr Trp Thr Gly Gly Asp Phe Val Ser Ser Asp Lys Val Ile
            260                 265                 270

Ile Trp Thr Glu Asn Gly Gln Ser Tyr Ile Tyr Lys Leu Pro Ala Ser
        275                 280                 285

Cys Leu Pro Ala Ser Asp Ser Phe Arg Ser Asp Val Gly Lys Ala Val
    290                 295                 300

Glu Asn Leu Ile Pro Pro Val Gln His Ile Leu Leu Asp Arg Lys Asp
305                 310                 315                 320

Lys Glu Leu Leu Ile Cys Pro Pro Val Thr Arg Phe Phe Tyr Gly Cys
                325                 330                 335

Arg Glu Tyr Phe His Lys Leu Leu Ile Gln Gly Asp Ser Ser Gly Arg
            340                 345                 350

Leu Asn Ile Trp Asn Ile Ser Asp Thr Ala Asp Lys Gln Gly Ser Glu
```

-continued

```
              355                 360                 365
Glu Gly Leu Ala Met Thr Thr Ser Ile Ser Leu Gln Glu Ala Phe Asp
            370                 375                 380
Lys Leu Asn Pro Cys Pro Ala Gly Ile Ile Asp Gln Leu Ser Val Ile
385                 390                 395                 400
Pro Asn Ser Asn Glu Pro Leu Lys Val Thr Ala Ser Val Tyr Ile Pro
                405                 410                 415
Ala His Gly Arg Leu Val Cys Gly Arg Glu Asp Gly Ser Ile Val Ile
                420                 425                 430
Val Pro Ala Thr Gln Thr Ala Ile Val Gln Leu Leu Gln Gly Glu His
                435                 440                 445
Met Leu Arg Arg Gly Trp Pro Pro His Arg Thr Leu Arg Gly His Arg
            450                 455                 460
Asn Lys Val Thr Cys Leu Leu Tyr Pro His Gln Val Ser Ala Arg Tyr
465                 470                 475                 480
Asp Gln Arg Tyr Leu Ile Ser Gly Gly Val Asp Phe Ser Val Ile Ile
                485                 490                 495
Trp Asp Ile Phe Ser Gly Glu Met Lys His Ile Phe Cys Val His Gly
            500                 505                 510
Gly Glu Ile Thr Gln Leu Leu Val Pro Pro Glu Asn Cys Ser Ala Arg
            515                 520                 525
Val Gln His Cys Ile Cys Ser Val Ala Ser Asp His Ser Val Gly Leu
            530                 535                 540
Leu Ser Leu Arg Glu Lys Lys Cys Ile Met Leu Ala Ser Arg His Leu
545                 550                 555                 560
Phe Pro Ile Gln Val Ile Lys Trp Arg Pro Ser Asp Tyr Leu Val
                565                 570                 575
Val Gly Cys Ser Asp Gly Ser Val Tyr Val Trp Gln Met Asp Thr Gly
            580                 585                 590
Ala Leu Asp Arg Cys Val Met Gly Ile Thr Ala Val Glu Ile Leu Asn
            595                 600                 605
Ala Cys Asp Glu Ala Val Pro Ala Ala Val Asp Ser Leu Ser His Pro
610                 615                 620
Ala Val Asn Leu Lys Gln Ala Met Thr Arg Arg Ser Leu Ala Ala Leu
625                 630                 635                 640
Lys Asn Met Ala His His Lys Leu Gln Thr Leu Ala Thr Asn Leu Leu
                645                 650                 655
Ala Ser Glu Ala Ser Asp Lys Gly Asn Leu Pro Lys Tyr Ser His Asn
            660                 665                 670
Ser Leu Met Val Gln Ala Ile Lys Thr Asn Leu Thr Asp Pro Asp Ile
            675                 680                 685
His Val Leu Phe Phe Asp Val Glu Ala Leu Ile Ile Gln Leu Leu Thr
            690                 695                 700
Glu Glu Ala Ser Arg Pro Asn Thr Ala Leu Ile Ser Pro Glu Asn Leu
705                 710                 715                 720
Gln Lys Ala Ser Gly Ser Ser Asp Lys Gly Gly Ser Phe Leu Thr Gly
                725                 730                 735
Lys Arg Ala Ala Val Leu Phe Gln Gln Val Lys Glu Thr Ile Lys Glu
                740                 745                 750
Asn Ile Lys Glu His Leu Leu Asp Asp Glu Glu Asp Glu Glu Ile
            755                 760                 765
Met Arg Gln Arg Arg Glu Glu Ser Asp Pro Glu Tyr Arg Ser Ser Lys
770                 775                 780
```

```
Ser Lys Pro Leu Thr Leu Leu Glu Tyr Asn Leu Thr Met Asp Thr Ala
785                 790                 795                 800

Lys Leu Phe Met Ser Cys Leu His Ala Trp Gly Leu Asn Glu Val Leu
                805                 810                 815

Asp Glu Val Cys Leu Asp Arg Leu Gly Met Leu Lys Pro His Cys Thr
            820                 825                 830

Val Ser Phe Gly Leu Leu Ser Arg Gly Gly His Met Ser Leu Met Leu
        835                 840                 845

Pro Gly Tyr Asn Gln Pro Ala Cys Lys Leu Ser His Gly Lys Thr Glu
    850                 855                 860

Val Gly Arg Lys Leu Pro Ala Ser Glu Gly Val Gly Lys Gly Thr Tyr
865                 870                 875                 880

Gly Val Ser Arg Ala Val Thr Thr Gln His Leu Leu Ser Ile Ile Ser
                885                 890                 895

Leu Ala Asn Thr Leu Met Ser Met Thr Asn Ala Thr Phe Ile Gly Asp
            900                 905                 910

His Met Lys Lys Gly Pro Thr Arg Pro Arg Pro Ser Thr Pro Asp
        915                 920                 925

Leu Ser Lys Ala Arg Gly Ser Pro Thr Ser Ser Asn Ile Val Gln
    930                 935                 940

Gly Gln Ile Lys Gln Val Ala Ala Pro Val Ser Ala Arg Ser Asp
945                 950                 955                 960

Ala Asp His Ser Gly Ser Asp Pro Pro Ser Ala Pro Ala Leu His Thr
                965                 970                 975

Cys Phe Leu Val Asn Glu Gly Trp Ser Gln Leu Ala Ala Met His Cys
            980                 985                 990

Val Met Leu Pro Asp Leu Leu Gly Leu Asp Lys Phe Arg Pro Pro Leu
        995                 1000                1005

Leu Glu Met Leu Ala Arg Arg Trp Gln Asp Arg Cys Leu Glu Val Arg
    1010                1015                1020

Glu Ala Ala Gln Ala Leu Leu Leu Ala Glu Leu Arg Arg Ile Glu Gln
1025                1030                1035                1040

Ala Gly Arg Lys Glu Ala Ile Asp Ala Trp Ala Pro Tyr Leu Pro Gln
                1045                1050                1055

Tyr Ile Asp His Val Ile Ser Pro Gly Val Thr Ser Glu Ala Ala Gln
            1060                1065                1070

Thr Ile Thr Thr Ala Pro Asp Ala Ser Gly Pro Glu Ala Lys Val Gln
        1075                1080                1085

Glu Glu Glu His Asp Leu Val Asp Asp Ile Thr Thr Gly Cys Leu
    1090                1095                1100

Ser Ser Val Pro Gln Met Lys Lys Ile Ser Thr Ser Tyr Glu Arg
1105                1110                1115                1120

Arg Lys Gln Ala Thr Ala Ile Val Leu Leu Gly Val Ile Gly Ala Glu
                1125                1130                1135

Phe Gly Ala Glu Ile Glu Pro Pro Lys Leu Leu Thr Arg Pro Arg Ser
            1140                1145                1150

Ser Ser Gln Ile Pro Glu Gly Phe Gly Leu Thr Ser Gly Gly Ser Asn
        1155                1160                1165

Tyr Ser Leu Ala Arg His Thr Cys Lys Ala Leu Thr Phe Leu Leu Leu
    1170                1175                1180
```

-continued

```
Gln Pro Pro Ser Pro Lys Leu Pro Pro His Ser Thr Ile Arg Arg Thr
1185                1190                1195                1200

Ala Ile Asp Leu Ile Gly Arg Gly Phe Thr Val Trp Glu Pro Tyr Met
            1205                1210                1215

Asp Val Ser Ala Val Leu Met Gly Leu Leu Glu Leu Cys Ala Asp Ala
        1220                1225                1230

Glu Lys Gln Leu Ala Asn Ile Thr Met Gly Leu Pro Leu Ser Pro Ala
    1235                1240                1245

Ala Asp Ser Ala Arg Ser Ala Arg His Ala Leu Ser Leu Ile Ala Thr
1250                1255                1260

Ala Arg Pro Pro Ala Phe Ile Thr Thr Ile Ala Lys Glu Val His Arg
1265                1270                1275                1280

His Thr Ala Leu Ala Ala Asn Thr Gln Ser Gln Gln Asn Met His Thr
            1285                1290                1295

Thr Thr Leu Ala Arg Ala Lys Gly Glu Ile Leu Arg Val Ile Glu Ile
        1300                1305                1310

Leu Ile Glu Lys Met Pro Thr Asp Val Val Asp Leu Leu Val Glu Val
    1315                1320                1325

Met Asp Ile Ile Met Tyr Cys Leu Glu Gly Ser Leu Val Lys Lys Lys
1330                1335                1340

Gly Leu Gln Glu Cys Phe Pro Ala Ile Cys Arg Phe Tyr Met Val Ser
1345                1350                1355                1360

Tyr Tyr Glu Arg Asn His Arg Ile Ala Val Gly Ala Arg His Gly Ser
            1365                1370                1375

Val Ala Leu Tyr Asp Ile Arg Thr Gly Lys Cys Gln Thr Ile His Gly
        1380                1385                1390

His Lys Gly Pro Ile Thr Ala Val Ala Phe Ala Pro Asp Gly Arg Tyr
    1395                1400                1405

Leu Ala Thr Tyr Ser Asn Thr Asp Ser His Ile Ser Phe Trp Gln Met
1410                1415                1420

Asn Thr Ser Leu Leu Gly Ser Ile Gly Met Leu Asn Ser Ala Pro Gln
1425                1430                1435                1440

Leu Arg Cys Ile Lys Thr Tyr Gln Val Pro Pro Val Gln Pro Ala Ser
            1445                1450                1455

Pro Gly Ser His Asn Ala Leu Lys Leu Ala Arg Leu Ile Trp Thr Ser
        1460                1465                1470

Asn Arg Asn Val Ile Leu Met Ala His Asp Gly Lys Glu His Arg Phe
    1475                1480                1485

Met Val
    1490
```

<210> SEQ ID NO 3
<211> LENGTH: 34
<212> TYPE: DNA
<213> ORGANISM: Artificial Sequence
<220> FEATURE:
<223> OTHER INFORMATION: primer

<400> SEQUENCE: 3
atggcaggaa acagccttgt tctacccatt gttc        34

<210> SEQ ID NO 4
<211> LENGTH: 30
<212> TYPE: DNA
<213> ORGANISM: Artificial Sequence
<220> FEATURE:
<223> OTHER INFORMATION: primer

```
<400> SEQUENCE: 4
gttgtcattg ccagcccttc ttcacttccc                                          30
```